United States Patent [19]

Guesdon et al.

[11] Patent Number: 5,650,272
[45] Date of Patent: Jul. 22, 1997

[54] NUCLEOTIDE SEQUENCES WHICH HYBRIDIZE SPECIFICALLY WITH BACTERIAL STRAINS OF THE MYCOBACTERIUM AVIUM-INTRACELLULARE COMPLEX

[75] Inventors: Jean-Luc Guesdon, Sevres; Dominique Thierry, Boulogne; Veronique Vincent, Paris, all of France

[73] Assignee: Institut Pasteur, Paris, France

[21] Appl. No.: 232,015

[22] PCT Filed: Oct. 30, 1992

[86] PCT No.: PCT/FR92/01015

§ 371 Date: May 2, 1994

§ 102(e) Date: May 2, 1994

[87] PCT Pub. No.: WO93/09251

PCT Pub. Date: May 13, 1993

[30] Foreign Application Priority Data

Oct. 31, 1991 [FR] France ................... 91 13504

[51] Int. Cl.[6] ............ C12Q 1/68; C12N 15/63; C07H 21/04
[52] U.S. Cl. .............. 435/6; 435/320.1; 536/24.32; 536/24.33; 935/77; 935/78
[58] Field of Search ............ 536/24.32, 24.33; 435/6, 91.2, 320.1; 935/77, 78

[56] References Cited

U.S. PATENT DOCUMENTS 5,314,801  5/1994  Nycz et al. .................. 435/6
5,422,242  6/1995  Young ......................... 435/6

FOREIGN PATENT DOCUMENTS 0 288 306   10/1988  European Pat. Off. .
2 651 505    9/1989  France .
90/12875    11/1990  WIPO .

OTHER PUBLICATIONS

Baess et al. (1983) Path. Microbiol. Immunol. Scand. 91:201–203.
Saito et al. (1990, Aug.) J. Clin. Micro. 28(8):1694–1697.
Thierry et al. (1993) J. Clin. Micro. 31(5):1048–1054.
*Journal of Clinical Microbiology*, "Rapid Identification Using a Specific DNA Probe of *Mycobacterium avium* Complex from Patients with Acquired Immunodeficienty Syndrome", Kiehn, et al.; vol. 25, No. 8; Aug. 1987, pp. 1551–1552.
*Molecular Biology*, "Detection and Identification of Mycobacteria by Amplification of Mycobacterial DNA", Hance et al.; vol. 3, No. 7, 1989 pp. 843–849.

*Primary Examiner*—Lisa B. Arthur
*Attorney, Agent, or Firm*—Burns, Doane, Swecker & Mathis, L.L.P.

[57] ABSTRACT

A nucleic acid sequence which specifically hybridizes with a genomic nucleic acid sequence of strains of the complex *Mycobacterium avium-intracellulare* selected from nucleotide sequence SEQ ID No 1, nucleotide sequence SEQ ID No 2, complementary sequences thereof, and sequences differing therefrom by the mutation, insertion, deletion or substitution of one or more bases, but does not hybridize with the nucleic acids of mycobacteria which do not belong to said complex. Fragments of the sequence may be used as primers for amplifying sequences which are specific for strains of the complex *Mycobacterium avium-intracellulare*, and as nucleic probes which are specific for nucleic sequences of strains of the complex *Mycobacterium avium-intracellulare*. A method for detecting strains of the complex *Mycobacterium avium-intracellulare* in a biological sample, and a kit for implementing the method, are also provided.

17 Claims, 21 Drawing Sheets pair of primers no. 1:

5' ATGGCCGGGAGACGATCTATGCCGGCGTAC 3'

5' CGTTCGATCGCAGTTTGTGCAGCGCGTACA 3' pair of primers no. 2:

5' ATGGCCGGGAGACGATCTATGCCGGCGTAC 3'

5' AACACCCTGACCCGCAGCCGTTCGATCGCA 3' pair of primers no. 3:

5' ATGGCCGGGAGACGATCTATGCCGGCGTAC 3'

5' GAACACCCTGACCCGCAGCCGTTCGATCGC 3' pair of primers no. 4:

5' ATGGCCGGGAGACGATCTATGCCGGCGTAC 3'

5' CGAACACCCTGACCCGCAGCCGTTCGATCG 3' pair of primers no. 5:

5' GCCGGGAGACGATCTATGCCGGCGTACCGG 3'

5' CGTTCGATCGCAGTTTGTGCAGCGCGTACA 3' pair of primers no. 6

5' GCCGGGAGACGATCTATGCCGGCGTACCGG 3'

5' AACACCCTGACCCGCAGCCGTTCGATCGCA 3'

FIG. 1A pair of primers no. 7:

5' GCCGGGAGACGATCTATGCCGGCGTACCGG 3'

5' GAACACCCTGACCCGCAGCCGTTCGATCGC 3' pair of primers no. 8:

5' GCCGGGAGACGATCTATGCCGGCGTACCGG 3'

5' CGAACACCCTGACCCGCAGCCGTTCGATCG 3' pair of primers no. 9:

5' CCGGCCGAGGGCGACCGCCGGGACCTAACG 3'

5' CGTTCGATCGCAGTTTGTGCAGCGCGTACA 3' pair of primers no. 10:

5' CCGGCCGAGGGCGACCGCCGGGACCTAACG 3'

5' AACACCCTGACCCGCAGCCGTTCGATCCGA 3' pair of primers no. 11:

5' CCGGCCGAGGGCGACCGCCGGGACCTAACG 3'

5' GAACACCCTGACCCGCAGCCGTTCGATCGC 3' pair of primers no. 12:

5' CCGGCCGAGGGCGACCGCCGGGACCTAACG 3'

5' CGAACACCCTGACCCGCAGCCGTTCGATGC 3'

FIG. 1B pair of primers no. 13:

5' TCAACCGCTACCCCGGGGCCCGATGCGACG 3'

5' TCACCGTCCAGCGCAACTGCGCTTCGTCGA 3' pair of primers no. 14:

5' GCTACCCCGGGGCCCGATGCGACGTCGAGA 3'

5' TCACCGTCCAGCGCAACTGCGCTTCGTCGA 3' pair of primers no. 15 :

5' GCCCGCGTGAATTCCGCCGTGCTCGACGAA 3'

5' GACGCGCTTGCCGGTGAAGTCCACCGTTCG 3' pair of primers no. 16:

5' GCCCGCGTGAATTCCGCCGTGCTCGACGAA 3'

5' GGATCCCGTGCCAATGACGGCGACGCGCTT 3' pair of primers no. 17:

5' GCCCGCGTGAATTCCGCCGTGCTCGACGAA 3'

5' GATGCGGCCTCGGTCGAGTGATCGCGAATC 3' pair of primers no. 18:

5' GCCCGCGTGAATTCCGCCGTGCTCGACGAA 3'

5' CGATGCGGCCTCGGTCGAGTGATCGCGAAT 3'

FIG. 1C pair of primers no. 19:

5' GCCCGCGTGAATTCCGCCGTGCTCGACGAA 3'

5' GCGATGCGGCCTCGGTCGAGTGATCGCGAA 3' pair of primers no. 20:

5' GCCCGCGTGAATTCCGCCGTGCTCGACGAA 3'

5' TGCGATGCGGCCTCGGTCGAGTGATCGCGA 3' pair of primers no. 21:

5' GCCCGCGTGAATTCCGCCGTGCTCGACGAA 3'

5' CACGTACAGCTGCGATGCGGCCTCGGTCGA 3' pair of primers no. 22:

5' ACCACACCGCGGCCTGGCCGCACGAACGGT 3'

5' GCCACGATATCCGTCGTCGTTCCGCGTAAT 3' pair of primers no. 23:

5' ACGAACGGTGGACTTCACCGGCAACGCCGT 3'

5' GCCACGATATCCGTCGTCGTTCCGCGTAAT 3' pair of primers no. 24:

5' CCCGGGTCTGGCATCCAATCGAGATTCGCG 3'

5' GCCACGATATCCGTCGTCGTTCCGCGTAAT 3'

FIG. 1D pair of primers no. 25:

5' CCGGGTCTGGCATCCAATGCAGATTCGCGA 3'

5' GCCACGATATCCGTCGTCGTTCCGCGTAAT 3' pair of primers no. 26:

5' CGGGTCTGGCATCCAATGCAGATTCGCGAT 3'

5' GCCACGATATCCGTCGTCGTTCCGCGTAAT 3' pair of primers no. 27:

5' GGGTCTGGCATCCAATGCAGATTCGCGATC 3'

5' GCCACGATATCCGTCGTCGTTCCGCGTAAT 3' pair of primers no. 28:

5' TCCAATGCAGATTCGCGATCACTCGACCGA 3'

5' GCCACGATATCCGTCGTCGTTCCGCGTAAT 3'

FIG. 1E pair of primers no. 29:

5' CGGCATCGAGTGTCCGGGCCGGCGACCGTA 3'

5' ATCCGCCGCGATACACGACGACGGCGTTCG 3' pair of primers no. 30:

5' CGGCATCGAGTGTCCGGGCCGGCGACCGTA 3'

5' GCGCCGCGGGCTGGGATCCGCCGCGATACA 3' pair of primers no. 31:

5' CGGCATCGAGTGTCCGGGCCGGCGACCGTA 3'

5' CGCGCCGCGGGCTGGGATCCGCCGCGATAC 3' pair of primers no. 32:

5' CGGCATCGAGTGTCCGGGCCGGCGACCGTA 3'

5' GCGCGCCGCGGGCTGGGATCCGCCGCGATA 3' pair of primers no. 33:

5' CATCGAGTGTCCGGGCCGGCGACCGTATCG 3'

5' ATCCGCCGCGATACACGACGACGGCGTTCG 3' pair of primers no. 34:

5' CATCGAGTGTCCGGGCCGGCGACCGTATCG 3'

5' GCGCCGCGGGCTGGGATCCGCCGCGATACA 3'

FIG. 1F pair of primers no. 35:

5' CATCGAGTGTCCGGGCCGGCGACCGTATCG 3'

5' CGCGCCGCGGGCTGGGATCCGCCGCGATAC 3' pair of primers no. 36:

5' CATCGAGTGTCCGGGCCGGCGACCGTATCG 3'

5' GCGCGCCGCGGGCTGGGATCCGCCGCGATA 3' pair of primers no. 37:

5' ATCGAGTGTCCGGGCCGGCGACCGTATCGC 3'

5' ATCCGCCGCGATACACGACGACGGCGTTCG 3' pair of primers no. 38:

5' ATCGAGTGTCCGGGCCGGCGACCGTATCGC 3'

5' GCGCCGCGGGCTGGGATCCGCCGCGATACA 3' pair of primers no. 39:

5' ATCGAGTGTCCGGGCCGGCGACCGTATCGC 3'

5' CGCGCCGCGGGCTGGGATCCGCCGCGATAC 3' pair of primers no. 40:

5' ATCGAGTGTCCGGGCCGGCGACCGTATCGC 3'

5' GCGCCGCGGGCTGGGATCCGCCGCGATA 3'

FIG. 1G pair of primers no. 41:

5' TCGAGTGTCCGGGCCGGCGACCGTATCGCG 3'

5' ATCCGCCGCGATACACGACGACGGCGTTCG 3' pair of primers no. 42:

5' TCGAGTGTCCGGGCCGGCGACCGTATCGCG 3'

5' GCGCCGCGGGCTGGGATCCGCCGCGATACA 3' pair of primers no. 43:

5' TCGAGTGTCCGGGCCGGCGACCGTATCGCG 3'

5' CGCGCCGCGGGCTGGGATCCGCCGCGATAC 3' pair of primers no. 44:

5' TCGAGTGTCCGGGCCGGCGACCGTATCGCG 3'

5' GCGCGCCGCGGGCTGGGATCCGCCGCGATA 3' pair of primers no. 45:

5' CGAGTGTCCGGGCCGGCGACCGTATCGGCG 3'

5' ATCCGCCGCGATACACGACGACGGCGTTCG 3' pair of primers no. 46:

5' CGAGTGTCCGGGCCGGCGACCGTATCGGCG 3'

5' GCGCCGCGGGCTGGGATCCGCCGCGATACA 3'

FIG. 1H pair of primers no. 47:

5' CGAGTGTCCGGGCCGGCGACCGTATCGGCG 3'

5' CGCGCCGCGGGCTGGGATCCGCCGCGATAC 3' pair of primers no. 48:

5' CGAGTGTCCGGGCCGGCGACCGTATCGGCG 3'

5' GCGCGCCGCGGGCTGGGATCCGCCGCGATA 3' pair of primers no. 49:

5' CGCAACGACCTTCAAACCCGCGGCGTCGTA 3'

5' TCGAGGCCACCGCGCCGGGTTCCGATCGTC 3' pair of primers no. 50:

5' CGCAACGACCTTCAAACCCGCGGCGTCGTA 3'

5' GTCGAGGCCACCGCGCCGGGTTCCGATCGT 3' pair of primers no. 51:

5' TGCTCTGTAGCAATGCGATGCGCGGATCGA 3'

5' TCGAGGCCACCGCGCCGGGTTCCGATCGTC 3' pair of primers no. 52:

5' TGCTCTGTAGCAATGCGATGCGCGGATCGA 3'

5' GTCGAGGCCACCGCGCCGGGTTCCGATCGT 3'

FIG. 1I pair of primers no. 53:

5' TCGTAGCAATGCGATGCGCGGATCGACCGT 3'

5' TCGAGGCCACCGCGCCGGGTTCCGATCGTC 3' pair of primers no. 54:

5' TCGTAGCAATGCGATGCGCGGATCGACCGT 3'

5' GTCGAGGCCACCGCGCCGGGTTCCGATCGT 3' pair of primers no. 55:

5' GTAGCAATGCGATGCGCGGATCGACCGTCG 3'

5' TCGAGGCCACCGCGCCGGGTTCCGATCGTC 3' pair of primers no. 56:

5' GTAGCAATGCGATGCGCGGATCGACCGTCG 3'

5' GTCGAGGCCACCGCGCCGGGTTCCGATCGT 3' pair of primers no. 57:

5' CCACCACATTGCGGGTGACGAGTTCGATCG 3'

5' TCCCCTGAAAGTCGGCTTGCTCAACGACTA 3' pair of primers no. 58:

5' CCACCACATTGCGGGTGACGAGTTCGATCG 3'

5' TATGGCAGACGAGGTTCGCGCATACGGTTC 3'

FIG. 1J pair of primers no. 59:

5' CCACCACATTGCGGGTGACGAGTTCGATCG 3'

5' CTATGGCAGACGAGGTTCGCGCATACGGTT 3' pair of primers no. 60:

5' CCACCACATTGCGGGTGACGAGTTCGATCG 3'

5' CCGCTATGGCAGACGAGGTTCGCGCATACG 3' pair of primers no. 61:

5' CCACCACATTGCGGGTGACGAGTTCGATCG 3'

5' TGCCGCTATGGCAGACGAGGTTCGCGCATA 3' pair of primers no. 62:

5' CACCACATTGCGGGTGACGAGTTCGATCGG 3'

5' TCCCCTGAAAGTCGGCTTGCTCAACGACTA 3' pair of primers no. 63:

5' CACCACATTGCGGGTGACGAGTTCGATCGG 3'

5' TATGGCAGACGAGGTTCGCGCATACGGTTC 3' pair of primers no. 64:

5' CACCACATTGCGGGTGACGAGTTCGATCGG 3'

5' CTATGGCAGACGAGGTTCGCGCATACGGTT 3'

FIG. 1K pair of primers no. 65:

5' CACCACATTGCGGGTGACGAGTTCGATCGG 3'

5' CCGCTATGGCAGACGAGGTTCGCGCATACG 3' pair of primers no. 66:

5' CACCACATTGCGGGTGACGAGTTCGATCGG 3'

5' TGCCGCTATGGCAGACGAGGTTCGCGCATA 3' pair of primers no. 67:

5' CTGTCGTTGTCGGTGTCGCCGGACGTCGAA 3'

5' GATTGACGGCGCGTGGGACTCCTGCGTCGA 3' pair of primers no. 68:

5' TGTCGTTGTCGGTGTCGCCGGACGTCGGAT 3'

5' GATTGACGGCGCGTGGGACTCCTGCGTCGA 3' pair of primers no. 69:

5' GTCGGTGTCGCCGGACGTCGGATAGTCGTT 3'

5' GATTGACGGCGCGTGGGACTCCTGCGTCGA 3' pair of primers no. 70:

5' GCCGACTTTCAGGGGAGCGACCGAACCGTA 3'

5' GATTGACGGCGCGTGGGACTCCTGCGTCGA 3'

FIG. 1L pair of primers no. 71:

5' GCCGACTTTCAGGGGAGCGACCGAACCGTA 3'

5' AAGTGGCGCAGTGCGATCGTGCCGACATTA 3' pair of primers no. 72:

5' CCGACTTTCAGGGGAGCGACCGAACCGTAT 3'

5' GATTGACGGCGCGTGGGACTCCTGCGTCGA 3' pair of primers no. 73:

5' CCGACTTTCAGGGGAGCGACCGAACCGTAT 3'

5' AAGTGGCGCAGTGCGATCGTGCCGACATTA 3' pair of primers no. 74:

5' ACTTTCAGGGGAGCGACCGAACCGTATGCG 3'

5' GATTGACGGCGCGTGGGACTCCTGCGTCGA 3' pair of primers no. 75:

5' ACTTTCAGGGGAGCGACCGAACCGTATGCG 3'

5' AAGTGGCGCAGTGCGATCGTGCCGACATTA 3' pair of primers no. 76:

5' TTTCAGGGGAGCGACCGAACCGTATGCGCG 3'

5' GATTGACGGCGCGTGGGACTCCTGCGTCGA 3'

FIG. 1M pair of primers no. 77:

5' TTTCAGGGGAGCGACCGAACCGTATGCGCG 3'

5' AAGTGGCGCAGTGCGATCGTGCCGACATTA 3' pair of primers no. 78:

5' GGAGACGGAATGAACGCTCACATCGACGCA 3'

5' CGTTCCCTACCGACCTTCTCCGGGCGATTA 3' pair of primers no. 79:

5' GGAGACGGAATGAACGCTCACATCGACGCA 3'

5' TTATCGGTGGTTGCGTGTACCCCGATCCGG 3'

FIG. 1N

SEQUENCE LISTING ( 1 ) GENERAL INFORMATION:

( i i i ) NUMBER OF SEQUENCES: 66

( 2 ) INFORMATION FOR SEQ ID NO:1:

( i ) SEQUENCE CHARACTERISTICS:
( A ) LENGTH: 2004 base pairs
( B ) TYPE: nucleic acid
( C ) STRANDEDNESS: single
( D ) TOPOLOGY: linear ( i i ) MOLECULE TYPE: cDNA ( i i i ) HYPOTHETICAL: NO ( i v ) ANTI-SENSE: NO ( v i ) ORIGINAL SOURCE:
( A ) ORGANISM: Mycobacterium avium ( x i ) SEQUENCE DESCRIPTION: SEQ ID NO:1:

| | | | | | | |
|---|---|---|---|---|---|---|
| GTCGACGCCA | CCACACTGCC | CCACGACATC | GAACGTCCTG | GCCGGCACGA | TCGCGAAGGC | 60 |
| GGGAACGGTT | GTCGGGCAGC | GAATTCTCGT | GGGTCGGCCA | CTGGTCGGGA | ACGCCCGTTG | 120 |
| GCTGGCCATT | CACGAAGGAG | TGGGTGCTCA | CCCGCGAACC | TTCCACAATG | GGGCATGGCT | 180 |
| CCATTGGCGC | CGGCGAAAA | GGACGCCGCT | GATCCGCGCG | GTCATCAAAG | GTGAGCCCAG | 240 |
| CTTTGAACTC | CAGCTCGACG | TGGCATTCGA | CGGCGCGCCA | TCGAACGGGC | CAGCACGCCA | 300 |
| TGCCAGGTCA | CCTGATGATC | GCGAATGAAG | CGCGGTTCGC | GCCATACCGT | ACGTGCTGGC | 360 |
| CCGGCCACCC | GGTGTCGTGA | CAGCACCGGT | GTTCGGCGCG | ATCCAACTAG | CCTGAGGCAC | 420 |
| CACCGACCGC | GCGGGCGATG | TGGTTCGCTG | GGCGCCGCAT | GGAAAACGTG | CGCGCTGCCG | 480 |
| TCGGGCAAAA | CCTTCGGGCC | ACGAGATTAA | TCGGAACCCA | TCCACCCCTG | TCGGATGAAC | 540 |
| CGGTCCGAAT | TCGCAGGTAA | CGTTCCCGGC | GCGCCTGCTG | GCCGACGGGA | ACGAGCCTTT | 600 |
| CACCTGCTCC | ATTCCCGTTC | TTCACACCCT | CCCCGGTTCA | ACGGCCGTGC | CGCGGCGAGA | 660 |
| CCACGCACGA | TCACGGTGGC | CGCGTCGTGC | GACAGGCCCG | GCATCGAGTG | TCCGGGCCGG | 720 |
| CGACCGTATC | GCGCCTCGAA | GCGGTCGAGG | AAGGCCTGTC | CGACCGTGTT | GCGCTCGTCG | 780 |
| TAGCTGTCCA | GGCCGATCCA | TCCGGATAGG | TGCCGCCTCC | ACTCCGCGCT | GATGTGTGCC | 840 |
| ATTTCGAACG | CCGTCGTCGT | GTATCGCGGC | GGATCCCAGC | CCGCGGCGCG | CAGCGCATCC | 900 |
| GTGAAGCCCC | ACAGCCCGTG | CCCGAACCCG | AACGTGCACC | AGCCGTCGGG | TTCGCCGCA | 960 |
| CGCAACGCAG | TGACCGTCTC | GGACTTGTCG | GCTTCGACCT | GGGGAATCGC | CACGGTCGCA | 1020 |
| ACGACCTTCA | AACCCGCGGC | GTCGTAGGCT | CTCTCGGCGA | AGGCGAGGTA | CCTCCTTACC | 1080 |
| GATGAGCGAT | GCCTCGTAGC | AATGCGATGC | GCGGATCGAC | CGTCGCCGGA | TCATCACCGC | 1140 |
| GGCCAGCATC | ACCGGCTCCT | CGGGCATCGA | GCCGTTGTTC | AGTCGAAGCA | CCAGTCGCCG | 1200 |
| AGCGCTCCCT | CCGATCCCGA | CAGAGTGACG | ATCGGAACCC | GGCGCGGTGG | CCTCGACGTG | 1260 |
| GGAACGCAGC | GGCACCACGT | TATCCGACAC | CCACGGGCCC | GAAGATCGCC | AGGCAACCCT | 1320 |
| CCGCGACGAG | CTCGTCGAAG | GCCCGCTCCG | ACCACTTGGT | AGGTCCCGTT | GGGCAGGCCC | 1380 |
| ACCACATTGC | GGGTGACGAG | TTCGATCGGC | CGGTCGATCA | GTCCCGAGGA | AAGGGCTTCA | 1440 |
| TCCATCACCA | GCCGCAGCGC | CGACGCTGTC | GTTGTCGGTG | TCGCCGGACG | TCGGATAGTC | 1500 |
| GTTGAGCAAG | CCGACTTTCA | GGGGAGCGAC | CGAACCGTAT | GCGCGAACCT | CGTCTGCCAT | 1560 |
| AGCGGCAACA | TACAGATATG | GAGGTTGAGG | CCCACCGCGC | CACCGCAAAC | TCGCACCCGC | 1620 |

| | | | | | |
|---|---|---|---|---|---|
|CGAAAATGGT|GGTTTACGAA|AAGTGCAAAG|CGAACTTTCG|GCATGTTAGT|TTTTCCGAGC|1680|
|GGGGGATCAC|ATTCCGGAGG|AGACGGAATG|AACGCTCACA|TCGACGCAGG|AGTCCCACGC|1740|
|GCCGTCAATC|CAGAAGAAGT|ACCGCGTGAT|CCAGTGGGGC|ATGGGTAATG|TCGGCACGAT|1800|
|CGCACTGCGC|CACTTCGCAC|ACAACCCTCT|CTACGAAGTG|GTCGGAGTGC|TTTGTAATCG|1860|
|CCCGGAGAAG|GTCGGTAGGG|AACGCCGGTG|AACTTCGTCG|GGGTAGGACC|GGATCGGGGT|1920|
|ACACGCAACC|ACCGATAAGG|CCACCTTGGA|GACACTCGAC|AGCCGATTGC|GTGTTCTACG|1980|
|CGCCGCTCTG|GTCCGGACGT|CGAC| | |2004|

(2) INFORMATION FOR SEQ ID NO: 2:

(i) SEQUENCE CHARACTERISTICS:
        (A) LENGTH: 1642 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iii) ANTI-SENSE: NO (vi) ORIGINAL SOURCE:
        (A) ORGANISM: Mycobacterium avium (xi) SEQUENCE DESCRIPTION: SEQ ID NO: 2:

| | | | | | |
|---|---|---|---|---|---|
|GACCAGTTCC|GCGTGCATTC|GCCCGCCCAC|CTCGCCGACC|AGCGAGGCCG|TGTGGTCGAG|60|
|ATCGTCGGGT|GTGCTGGGCG|AACCATCAC|CGTGTCCACC|GGTCCGCACA|GGTCGAGGGC|120|
|CACGATGTCG|GCGCCCTCCT|GCGCGAACCG|CACGGCTTGG|GCGCGCCCGA|TTCCCCGCGC|180|
|CGCGCCCGTG|ATCAACGCGA|CCTTCCCCGC|CAGCCGCCCC|GGACTGACTT|GTGGCATCCG|240|
|GCGATTCTGC|CGCGCGAGCG|GCACCGGGGT|CGGTGTGTGT|CCGATGGCCG|GGAGACGATC|300|
|TATGCCGGCG|TACCGGTCAC|CGGGATATCC|CGGCCGAGGG|CGACCGCCGG|GACCTAACGT|360|
|AGGCATCCGT|GACCAGTGGC|AGTGACCGGC|GCGCAACCCC|GGACGTCGAT|GTGGTGGTCG|420|
|TCGGCGCGGC|TTCGCCGGCC|TGTACGCGCT|GCACAAACTG|CGATCGAACG|GCTGCGGGTC|480|
|AGGGTGTTCG|AGGCCGGGCC|GGACGTCGGC|GGAACCTGGT|ACTTCAACCG|CTACCCCGGG|540|
|GCCCGATGCG|ACGTCGAGAG|CGTGGACTAC|TGCTACTCGT|TCTCCGACGC|GCTGCAGCGG|600|
|GAGTGGGATT|GGTCGGAGAA|GTACGCCACC|CAACCCGAGA|TTCTGGCCTA|CATCAATTGG|660|
|GTCGCCGACC|GGCTGGATCT|GCGCCGCGAC|ATCACCCTGA|ACGCCCGCGT|GAATTCCGCC|720|
|GTGCTCGACG|AAGCGCAGTT|GCGCTGGACG|GTGACCACCG|AGACGGGCGA|GCGCGTCACC|780|
|GCCCGGTTCT|GCGTGATGGC|CACCGGCCCG|TTGTCGGCGG|CGATGACTCC|GCCGTTCCCC|840|
|GGTTTGGATA|CCTTCGCCGG|GCAGGTCTAC|CACACCGCGG|CCTGGCCGCA|CGAACGGTGG|900|
|ACTTCACCGG|CAAGCGCGTC|GCCGTCATTG|GCACGGGATC|CCCGGGTCTG|GCATCCAATG|960|
|CAGATTCGCG|ATCACTCGAC|CGAGGCCGCA|TCGCAGCTGT|ACGTGTTCCA|GCGCACCCCG|1020|
|AATTACAGTG|TGCCGGCGGG|TAACCGGCCG|TTGAGTGACT|CCGACCGTGC|CGAGGTGAAG|1080|
|GCCCATTACG|CGGAACGACG|ACGGATATCG|TGGCGCACGG|GGGCGGCTC|GCCCACGTCG|1140|
|CCCACCCGAA|GTTGACGATG|GAGGCAACCC|CCGAGGAACG|GCGTGAGGCA|TTCGAAAAGC|1200|
|GCTGGGAGCT|CGGCGAGTGC|TGTTCTCCAA|GACATTCGCC|GACCAGATGA|TCGACCCGGT|1260|
|CGCCAACGAG|GAGGCCCGCA|AGTTCTACGA|GGAGAAGGTG|CGCGCGGTCA|TCGACGACCC|1320|
|GGTGCTGGCC|GACCTGCTCA|TCCCGAATGA|CCATCCGATC|GGCACCAAGC|GAATCTGCAC|1380|

-continued

```
CGACAGCAAC TACTTTCAGA CCTTCAACCG CCCGAACGTG AAGCTGATCA GCGTCCGCAA      1440

GACGCCGATC ATGTCCATCG ATGCGACCGG CATTAACACC ACCGACGCCC ATTACGACCT      1500

CGACGCGATC GTGCTGGCGA CCGGATTCGA CGCGATGACC GGCGCGCTGG CCAAGATCGA      1560

CATCGTGGGC CGCGACGGAA GGCGGCTGAG CGACGACTGG TCCGGCGGGC CCCGCACGTA      1620

CCTGGGCCTC GGCGTCGACC TG                                              1642
```

( 2 ) INFORMATION FOR SEQ ID NO: 3:

( i ) SEQUENCE CHARACTERISTICS:
        ( A ) LENGTH: 30 base pairs
        ( B ) TYPE: nucleic acid
        ( C ) STRANDEDNESS: single
        ( D ) TOPOLOGY: linear ( i i ) MOLECULE TYPE: cDNA ( i i i ) HYPOTHETICAL: NO ( i i i ) ANTI-SENSE: NO ( v i ) ORIGINAL SOURCE:
        ( A ) ORGANISM: Mycobacterium avium ( x i ) SEQUENCE DESCRIPTION: SEQ ID NO: 3:

```
ATGGCCGGGA GACGATCTAT GCCGGCGTAC                                        30
```

( 2 ) INFORMATION FOR SEQ ID NO: 4:

( i ) SEQUENCE CHARACTERISTICS:
        ( A ) LENGTH: 30 base pairs
        ( B ) TYPE: nucleic acid
        ( C ) STRANDEDNESS: single
        ( D ) TOPOLOGY: linear ( i i ) MOLECULE TYPE: cDNA ( i i i ) HYPOTHETICAL: NO ( i i i ) ANTI-SENSE: NO ( v i ) ORIGINAL SOURCE:
        ( A ) ORGANISM: Mycobacterium avium ( x i ) SEQUENCE DESCRIPTION: SEQ ID NO: 4:

```
CGTTCGATCG CAGTTTGTGC AGCGCGTACA                                        30
```

( 2 ) INFORMATION FOR SEQ ID NO: 5:

( i ) SEQUENCE CHARACTERISTICS:
        ( A ) LENGTH: 30 base pairs
        ( B ) TYPE: nucleic acid
        ( C ) STRANDEDNESS: single
        ( D ) TOPOLOGY: linear ( i i ) MOLECULE TYPE: cDNA ( i i i ) HYPOTHETICAL: NO ( i i i ) ANTI-SENSE: NO ( v i ) ORIGINAL SOURCE:
        ( A ) ORGANISM: Mycobacterium avium ( x i ) SEQUENCE DESCRIPTION: SEQ ID NO: 5:

```
AACACCCTGA CCCGCAGCCG TTCGATCGCA                                        30
```

( 2 ) INFORMATION FOR SEQ ID NO: 6:

( i ) SEQUENCE CHARACTERISTICS:
    ( A ) LENGTH: 30 base pairs
    ( B ) TYPE: nucleic acid
    ( C ) STRANDEDNESS: single
    ( D ) TOPOLOGY: linear ( i i ) MOLECULE TYPE: cDNA ( i i i ) HYPOTHETICAL: NO ( i i i ) ANTI-SENSE: NO ( v i ) ORIGINAL SOURCE:
    ( A ) ORGANISM: Mycobacterium avium ( x i ) SEQUENCE DESCRIPTION: SEQ ID NO: 6:

GAACACCCTG ACCCGCAGCC GTTCGATCGC     30

( 2 ) INFORMATION FOR SEQ ID NO: 7:

( i ) SEQUENCE CHARACTERISTICS:
        ( A ) LENGTH: 30 base pairs
        ( B ) TYPE: nucleic acid
        ( C ) STRANDEDNESS: single
        ( D ) TOPOLOGY: linear ( i i ) MOLECULE TYPE: cDNA ( i i i ) HYPOTHETICAL: NO ( i i i ) ANTI-SENSE: NO ( v i ) ORIGINAL SOURCE:
        ( A ) ORGANISM: Mycobacterium avium ( x i ) SEQUENCE DESCRIPTION: SEQ ID NO: 7:

CGAACACCCT GACCCGCAGC CGTTCGATCG     30

( 2 ) INFORMATION FOR SEQ ID NO: 8:

( i ) SEQUENCE CHARACTERISTICS:
        ( A ) LENGTH: 30 base pairs
        ( B ) TYPE: nucleic acid
        ( C ) STRANDEDNESS: single
        ( D ) TOPOLOGY: linear ( i i ) MOLECULE TYPE: cDNA ( i i i ) HYPOTHETICAL: NO ( i i i ) ANTI-SENSE: NO ( v i ) ORIGINAL SOURCE:
        ( A ) ORGANISM: Mycobacterium avium ( x i ) SEQUENCE DESCRIPTION: SEQ ID NO: 8:

GCCGGGAGAC GATCTATGCC GGCGTACCGG     30

( 2 ) INFORMATION FOR SEQ ID NO: 9:

( i ) SEQUENCE CHARACTERISTICS:
        ( A ) LENGTH: 30 base pairs
        ( B ) TYPE: nucleic acid
        ( C ) STRANDEDNESS: single
        ( D ) TOPOLOGY: linear ( i i ) MOLECULE TYPE: cDNA ( i i i ) HYPOTHETICAL: NO ( i i i ) ANTI-SENSE: NO ( v i ) ORIGINAL SOURCE:
        ( A ) ORGANISM: Mycobacterium avium ( x i ) SEQUENCE DESCRIPTION: SEQ ID NO: 9:

CCGGCCGAGG GCGACCGCCG GGACCTAACG  30

( 2 ) INFORMATION FOR SEQ ID NO: 10:

( i ) SEQUENCE CHARACTERISTICS:
  ( A ) LENGTH: 30 base pairs
  ( B ) TYPE: nucleic acid
  ( C ) STRANDEDNESS: single
  ( D ) TOPOLOGY: linear ( i i ) MOLECULE TYPE: cDNA ( i i i ) HYPOTHETICAL: NO ( i i i ) ANTI-SENSE: NO ( v i ) ORIGINAL SOURCE:
  ( A ) ORGANISM: Mycobacterium avium ( x i ) SEQUENCE DESCRIPTION: SEQ ID NO: 10:

TCAACCGCTA CCCCGGGGCC CGATGCGACG  30

( 2 ) INFORMATION FOR SEQ ID NO: 11:

( i ) SEQUENCE CHARACTERISTICS:
  ( A ) LENGTH: 30 base pairs
  ( B ) TYPE: nucleic acid
  ( C ) STRANDEDNESS: single
  ( D ) TOPOLOGY: linear ( i i ) MOLECULE TYPE: cDNA ( i i i ) HYPOTHETICAL: NO ( i i i ) ANTI-SENSE: NO ( v i ) ORIGINAL SOURCE:
  ( A ) ORGANISM: Mycobacterium avium ( x i ) SEQUENCE DESCRIPTION: SEQ ID NO: 11:

TCACCGTCCA GCGCAACTGC GCTTCGTCGA  30

( 2 ) INFORMATION FOR SEQ ID NO: 12:

( i ) SEQUENCE CHARACTERISTICS:
  ( A ) LENGTH: 30 base pairs
  ( B ) TYPE: nucleic acid
  ( C ) STRANDEDNESS: single
  ( D ) TOPOLOGY: linear ( i i ) MOLECULE TYPE: cDNA ( i i i ) HYPOTHETICAL: NO ( i i i ) ANTI-SENSE: NO ( v i ) ORIGINAL SOURCE:
  ( A ) ORGANISM: Mycobacterium avium ( x i ) SEQUENCE DESCRIPTION: SEQ ID NO: 12:

GCTACCCCGG GGCCCGATGC GACGTCGAGA  30

( 2 ) INFORMATION FOR SEQ ID NO: 13:

( i ) SEQUENCE CHARACTERISTICS:
  ( A ) LENGTH: 30 base pairs
  ( B ) TYPE: nucleic acid
  ( C ) STRANDEDNESS: single
  ( D ) TOPOLOGY: linear (i i) MOLECULE TYPE: cDNA (i i i) HYPOTHETICAL: NO (i i i) ANTI-SENSE: NO (v i) ORIGINAL SOURCE:
            (A) ORGANISM: Mycobacterium avium (x i) SEQUENCE DESCRIPTION: SEQ ID NO: 13:

GCCCGCGTGA ATTCGCCGT GCTCGACGAA                                30

(2) INFORMATION FOR SEQ ID NO: 14:

(i) SEQUENCE CHARACTERISTICS:
            (A) LENGTH: 30 base pairs
            (B) TYPE: nucleic acid
            (C) STRANDEDNESS: single
            (D) TOPOLOGY: linear (i i) MOLECULE TYPE: cDNA (i i i) HYPOTHETICAL: NO (i i i) ANTI-SENSE: NO (v i) ORIGINAL SOURCE:
            (A) ORGANISM: Mycobacterium avium (x i) SEQUENCE DESCRIPTION: SEQ ID NO: 14:

GACGCGCTTG CCGGTGAAGT CCACCGTTCG                               30

(2) INFORMATION FOR SEQ ID NO: 15:

(i) SEQUENCE CHARACTERISTICS:
            (A) LENGTH: 30 base pairs
            (B) TYPE: nucleic acid
            (C) STRANDEDNESS: single
            (D) TOPOLOGY: linear (i i) MOLECULE TYPE: cDNA (i i i) HYPOTHETICAL: NO (i i i) ANTI-SENSE: NO (v i) ORIGINAL SOURCE:
            (A) ORGANISM: Mycobacterium avium (x i) SEQUENCE DESCRIPTION: SEQ ID NO: 15:

GGATCCCTGC CAATGACGGC GACGCGCTTG                               30

(2) INFORMATION FOR SEQ ID NO: 16:

(i) SEQUENCE CHARACTERISTICS:
            (A) LENGTH: 30 base pairs
            (B) TYPE: nucleic acid
            (C) STRANDEDNESS: single
            (D) TOPOLOGY: linear (i i) MOLECULE TYPE: cDNA (i i i) HYPOTHETICAL: NO (i i i) ANTI-SENSE: NO (v i) ORIGINAL SOURCE:
            (A) ORGANISM: Mycobacterium avium (x i) SEQUENCE DESCRIPTION: SEQ ID NO: 16:

GATGCGGCCT CGGTCGAGTG ATCGCGAATC                               30

( 2 ) INFORMATION FOR SEQ ID NO: 17:

( i ) SEQUENCE CHARACTERISTICS:
        ( A ) LENGTH: 30 base pairs
        ( B ) TYPE: nucleic acid
        ( C ) STRANDEDNESS: single
        ( D ) TOPOLOGY: linear ( i i ) MOLECULE TYPE: cDNA ( i i i ) HYPOTHETICAL: NO ( i i i ) ANTI-SENSE: NO ( v i ) ORIGINAL SOURCE:
        ( A ) ORGANISM: Mycobacterium avium ( x i ) SEQUENCE DESCRIPTION: SEQ ID NO: 17:

CGATGCGGCC TCGGTCGAGT GATCGCGAAT                    30

( 2 ) INFORMATION FOR SEQ ID NO: 18:

( i ) SEQUENCE CHARACTERISTICS:
        ( A ) LENGTH: 30 base pairs
        ( B ) TYPE: nucleic acid
        ( C ) STRANDEDNESS: single
        ( D ) TOPOLOGY: linear ( i i ) MOLECULE TYPE: cDNA ( i i i ) HYPOTHETICAL: NO ( i i i ) ANTI-SENSE: NO ( v i ) ORIGINAL SOURCE:
        ( A ) ORGANISM: Mycobacterium avium ( x i ) SEQUENCE DESCRIPTION: SEQ ID NO: 18:

GCGATGCGGC CTCGGTCGAG TGATCGCGAA                    30

( 2 ) INFORMATION FOR SEQ ID NO: 19:

( i ) SEQUENCE CHARACTERISTICS:
        ( A ) LENGTH: 30 base pairs
        ( B ) TYPE: nucleic acid
        ( C ) STRANDEDNESS: single
        ( D ) TOPOLOGY: linear ( i i ) MOLECULE TYPE: cDNA ( i i i ) HYPOTHETICAL: NO ( i i i ) ANTI-SENSE: NO ( v i ) ORIGINAL SOURCE:
        ( A ) ORGANISM: Mycobacterium avium ( x i ) SEQUENCE DESCRIPTION: SEQ ID NO: 19:

TGCGATGCGG CCTCGGTCGA GTGATCGCGA                    30

( 2 ) INFORMATION FOR SEQ ID NO: 20:

( i ) SEQUENCE CHARACTERISTICS:
        ( A ) LENGTH: 30 base pairs
        ( B ) TYPE: nucleic acid
        ( C ) STRANDEDNESS: single
        ( D ) TOPOLOGY: linear ( i i ) MOLECULE TYPE: DNA (genomic)

( i i i ) HYPOTHETICAL: NO ( i i i ) ANTI-SENSE: NO ( v i ) ORIGINAL SOURCE:
    ( A ) ORGANISM: Mycobacterium avium ( x i ) SEQUENCE DESCRIPTION: SEQ ID NO: 20:

CACGTACAGC TGCGATGCGG CCTCGGTCGA    30

( 2 ) INFORMATION FOR SEQ ID NO: 21:

( i ) SEQUENCE CHARACTERISTICS:
        ( A ) LENGTH: 30 base pairs
        ( B ) TYPE: nucleic acid
        ( C ) STRANDEDNESS: single
        ( D ) TOPOLOGY: linear ( i i ) MOLECULE TYPE: cDNA ( i i i ) HYPOTHETICAL: NO ( i i i ) ANTI-SENSE: NO ( v i ) ORIGINAL SOURCE:
        ( A ) ORGANISM: Mycobacterium avium ( x i ) SEQUENCE DESCRIPTION: SEQ ID NO: 21:

ACCACACCGC GGCCTGGCCG CACGAACGGT    30

( 2 ) INFORMATION FOR SEQ ID NO: 22:

( i ) SEQUENCE CHARACTERISTICS:
        ( A ) LENGTH: 30 base pairs
        ( B ) TYPE: nucleic acid
        ( C ) STRANDEDNESS: single
        ( D ) TOPOLOGY: linear ( i i ) MOLECULE TYPE: cDNA ( i i i ) HYPOTHETICAL: NO ( i i i ) ANTI-SENSE: NO ( v i ) ORIGINAL SOURCE:
        ( A ) ORGANISM: Mycobacterium avium ( x i ) SEQUENCE DESCRIPTION: SEQ ID NO: 22:

GCCACGATAT CCGTCGTCGT TCCGCGTAAT    30

( 2 ) INFORMATION FOR SEQ ID NO: 23:

( i ) SEQUENCE CHARACTERISTICS:
        ( A ) LENGTH: 30 base pairs
        ( B ) TYPE: nucleic acid
        ( C ) STRANDEDNESS: single
        ( D ) TOPOLOGY: linear ( i i ) MOLECULE TYPE: cDNA ( i i i ) HYPOTHETICAL: NO ( i i i ) ANTI-SENSE: NO ( v i ) ORIGINAL SOURCE:
        ( A ) ORGANISM: Mycobacterium avium ( x i ) SEQUENCE DESCRIPTION: SEQ ID NO: 23:

ACGAACGGTG GACTTCACCG GCAACGCCGT    30

( 2 ) INFORMATION FOR SEQ ID NO: 24:

( i ) SEQUENCE CHARACTERISTICS:
        ( A ) LENGTH: 30 base pairs
        ( B ) TYPE: nucleic acid
        ( C ) STRANDEDNESS: single ( D ) TOPOLOGY: linear ( i i ) MOLECULE TYPE: cDNA ( i i i ) HYPOTHETICAL: NO ( i i i ) ANTI-SENSE: NO ( v i ) ORIGINAL SOURCE:
    ( A ) ORGANISM: Mycobacterium avium ( x i ) SEQUENCE DESCRIPTION: SEQ ID NO: 24:

CCCGGGTCTG GCATCCAATC GAGATTCGCG     30

( 2 ) INFORMATION FOR SEQ ID NO: 25:

( i ) SEQUENCE CHARACTERISTICS:
        ( A ) LENGTH: 30 base pairs
        ( B ) TYPE: nucleic acid
        ( C ) STRANDEDNESS: single
        ( D ) TOPOLOGY: linear ( i i ) MOLECULE TYPE: cDNA ( i i i ) HYPOTHETICAL: NO ( i i i ) ANTI-SENSE: NO ( v i ) ORIGINAL SOURCE:
        ( A ) ORGANISM: Mycobacterium avium ( x i ) SEQUENCE DESCRIPTION: SEQ ID NO: 25:

CCGGGTCTGG CATCCAATGC AGATTCGCGA     30

( 2 ) INFORMATION FOR SEQ ID NO: 26:

( i ) SEQUENCE CHARACTERISTICS:
        ( A ) LENGTH: 30 base pairs
        ( B ) TYPE: nucleic acid
        ( C ) STRANDEDNESS: single
        ( D ) TOPOLOGY: linear ( i i ) MOLECULE TYPE: cDNA ( i i i ) HYPOTHETICAL: NO ( i i i ) ANTI-SENSE: NO ( v i ) ORIGINAL SOURCE:
        ( A ) ORGANISM: Mycobacterium avium ( x i ) SEQUENCE DESCRIPTION: SEQ ID NO: 26:

CGGGTCTGGC ATCCAATGCA GATTCGCGAT     30

( 2 ) INFORMATION FOR SEQ ID NO: 27:

( i ) SEQUENCE CHARACTERISTICS:
        ( A ) LENGTH: 30 base pairs
        ( B ) TYPE: nucleic acid
        ( C ) STRANDEDNESS: single
        ( D ) TOPOLOGY: linear ( i i ) MOLECULE TYPE: cDNA ( i i i ) HYPOTHETICAL: NO ( i i i ) ANTI-SENSE: NO ( v i ) ORIGINAL SOURCE:
        ( A ) ORGANISM: Mycobacterium avium ( x i ) SEQUENCE DESCRIPTION: SEQ ID NO: 27:

GGGTCTGGCA TCCAATGCAG ATTCGCGATC     30

( 2 ) INFORMATION FOR SEQ ID NO: 28:

( i ) SEQUENCE CHARACTERISTICS:
        ( A ) LENGTH: 30 base pairs
        ( B ) TYPE: nucleic acid
        ( C ) STRANDEDNESS: single
        ( D ) TOPOLOGY: linear ( i i ) MOLECULE TYPE: cDNA ( i i i ) HYPOTHETICAL: NO ( i i i ) ANTI-SENSE: NO ( v i ) ORIGINAL SOURCE:
        ( A ) ORGANISM: Mycobacterium avium ( x i ) SEQUENCE DESCRIPTION: SEQ ID NO: 28:

TCCAATGCAG ATTCGCATCA CTCGACCGAG                                                    30

( 2 ) INFORMATION FOR SEQ ID NO: 29:

( i ) SEQUENCE CHARACTERISTICS:
        ( A ) LENGTH: 30 base pairs
        ( B ) TYPE: nucleic acid
        ( C ) STRANDEDNESS: single
        ( D ) TOPOLOGY: linear ( i i ) MOLECULE TYPE: cDNA ( i i i ) HYPOTHETICAL: NO ( i i i ) ANTI-SENSE: NO ( v i ) ORIGINAL SOURCE:
        ( A ) ORGANISM: Mycobacterium avium ( x i ) SEQUENCE DESCRIPTION: SEQ ID NO: 29:

CGGCATCGAG TGTCCGGGCC GGCGACCGTA                                                    30

( 2 ) INFORMATION FOR SEQ ID NO: 30:

( i ) SEQUENCE CHARACTERISTICS:
        ( A ) LENGTH: 30 base pairs
        ( B ) TYPE: nucleic acid
        ( C ) STRANDEDNESS: single
        ( D ) TOPOLOGY: linear ( i i ) MOLECULE TYPE: cDNA ( i i i ) HYPOTHETICAL: NO ( i i i ) ANTI-SENSE: NO ( v i ) ORIGINAL SOURCE:
        ( A ) ORGANISM: Mycobacterium avium ( x i ) SEQUENCE DESCRIPTION: SEQ ID NO: 30:

ATCCGCCGCG ATACACGACG ACGGCGTTCG                                                    30

( 2 ) INFORMATION FOR SEQ ID NO: 31:

( i ) SEQUENCE CHARACTERISTICS:
        ( A ) LENGTH: 30 base pairs
        ( B ) TYPE: nucleic acid
        ( C ) STRANDEDNESS: single
        ( D ) TOPOLOGY: linear ( i i ) MOLECULE TYPE: cDNA ( i i i ) HYPOTHETICAL: NO ( i i i ) ANTI-SENSE: NO ( v i ) ORIGINAL SOURCE:
    ( A ) ORGANISM: Mycobacterium avium ( x i ) SEQUENCE DESCRIPTION: SEQ ID NO: 31:

GCGCCGCGGG CTGGGATCCG CCGCGATACA                         30

( 2 ) INFORMATION FOR SEQ ID NO: 32:

( i ) SEQUENCE CHARACTERISTICS:
        ( A ) LENGTH: 30 base pairs
        ( B ) TYPE: nucleic acid
        ( C ) STRANDEDNESS: single
        ( D ) TOPOLOGY: linear ( i i ) MOLECULE TYPE: cDNA ( i i i ) HYPOTHETICAL: NO ( i i i ) ANTI-SENSE: NO ( v i ) ORIGINAL SOURCE:
        ( A ) ORGANISM: Mycobacterium avium ( x i ) SEQUENCE DESCRIPTION: SEQ ID NO: 32:

CGCGCCGCGG GCTGGGATCC GCCGCGATAC                         30

( 2 ) INFORMATION FOR SEQ ID NO: 33:

( i ) SEQUENCE CHARACTERISTICS:
        ( A ) LENGTH: 30 base pairs
        ( B ) TYPE: nucleic acid
        ( C ) STRANDEDNESS: single
        ( D ) TOPOLOGY: linear ( i i ) MOLECULE TYPE: cDNA ( i i i ) HYPOTHETICAL: NO ( i i i ) ANTI-SENSE: NO ( v i ) ORIGINAL SOURCE:
        ( A ) ORGANISM: Mycobacterium avium ( x i ) SEQUENCE DESCRIPTION: SEQ ID NO: 33:

GCGCGCCGCG GGCTGGGATC CGCCGCGATA                         30

( 2 ) INFORMATION FOR SEQ ID NO: 34:

( i ) SEQUENCE CHARACTERISTICS:
        ( A ) LENGTH: 30 base pairs
        ( B ) TYPE: nucleic acid
        ( C ) STRANDEDNESS: single
        ( D ) TOPOLOGY: linear ( i i ) MOLECULE TYPE: cDNA ( i i i ) HYPOTHETICAL: NO ( i i i ) ANTI-SENSE: NO ( v i ) ORIGINAL SOURCE:
        ( A ) ORGANISM: Mycobacterium avium ( x i ) SEQUENCE DESCRIPTION: SEQ ID NO: 34:

CATCGAGTGT CCGGGCCGGC GACCGTATCG                         30

( 2 ) INFORMATION FOR SEQ ID NO: 35:

( i ) SEQUENCE CHARACTERISTICS:
        ( A ) LENGTH: 30 base pairs (B) TYPE: nucleic acid
(C) STRANDEDNESS: single
(D) TOPOLOGY: linear (ii) MOLECULE TYPE: cDNA (iii) HYPOTHETICAL: NO (iii) ANTI-SENSE: NO (vi) ORIGINAL SOURCE:
(A) ORGANISM: Mycobacterium avium (xi) SEQUENCE DESCRIPTION: SEQ ID NO: 35:

ATCGAGTGTC CGGGCCGGCG ACCGTATCGC  30

(2) INFORMATION FOR SEQ ID NO: 36:

(i) SEQUENCE CHARACTERISTICS:
(A) LENGTH: 30 base pairs
(B) TYPE: nucleic acid
(C) STRANDEDNESS: single
(D) TOPOLOGY: linear (ii) MOLECULE TYPE: cDNA (iii) HYPOTHETICAL: NO (iii) ANTI-SENSE: NO (vi) ORIGINAL SOURCE:
(A) ORGANISM: Mycobacterium avium (xi) SEQUENCE DESCRIPTION: SEQ ID NO: 36:

TCGAGTGTCC GGGCCGGCGA CCGTATCGCG  30

(2) INFORMATION FOR SEQ ID NO: 37:

(i) SEQUENCE CHARACTERISTICS:
(A) LENGTH: 30 base pairs
(B) TYPE: nucleic acid
(C) STRANDEDNESS: single
(D) TOPOLOGY: linear (ii) MOLECULE TYPE: cDNA (iii) HYPOTHETICAL: NO (iii) ANTI-SENSE: NO (vi) ORIGINAL SOURCE:
(A) ORGANISM: Mycobacterium avium (xi) SEQUENCE DESCRIPTION: SEQ ID NO: 37:

CGAGTGTCCG GCCGGCGAC CGTATCGGCG  30

(2) INFORMATION FOR SEQ ID NO: 38:

(i) SEQUENCE CHARACTERISTICS:
(A) LENGTH: 30 base pairs
(B) TYPE: nucleic acid
(C) STRANDEDNESS: single
(D) TOPOLOGY: linear (ii) MOLECULE TYPE: cDNA (iii) HYPOTHETICAL: NO (iii) ANTI-SENSE: NO (vi) ORIGINAL SOURCE:
(A) ORGANISM: Mycobacterium avium (xi) SEQUENCE DESCRIPTION: SEQ ID NO: 38:

CGCAACGACC TTCAAACCCG CGGCGTCGTA 30

( 2 ) INFORMATION FOR SEQ ID NO: 39:

( i ) SEQUENCE CHARACTERISTICS:
        ( A ) LENGTH: 30 base pairs
        ( B ) TYPE: nucleic acid
        ( C ) STRANDEDNESS: single
        ( D ) TOPOLOGY: linear ( i i ) MOLECULE TYPE: cDNA ( i i i ) HYPOTHETICAL: NO ( i i i ) ANTI-SENSE: NO ( v i ) ORIGINAL SOURCE:
        ( A ) ORGANISM: Mycobacterium avium ( x i ) SEQUENCE DESCRIPTION: SEQ ID NO: 39:

TCGAGGCCAC CGCGCCGGGT TCCGATCGTC 30

( 2 ) INFORMATION FOR SEQ ID NO: 40:

( i ) SEQUENCE CHARACTERISTICS:
        ( A ) LENGTH: 30 base pairs
        ( B ) TYPE: nucleic acid
        ( C ) STRANDEDNESS: single
        ( D ) TOPOLOGY: linear ( i i ) MOLECULE TYPE: cDNA ( i i i ) HYPOTHETICAL: NO ( i i i ) ANTI-SENSE: NO ( v i ) ORIGINAL SOURCE:
        ( A ) ORGANISM: Mycobacterium avium ( x i ) SEQUENCE DESCRIPTION: SEQ ID NO: 40:

GTCGAGGCCA CCGCGCCGGG TTCCGATCGT 30

( 2 ) INFORMATION FOR SEQ ID NO: 41:

( i ) SEQUENCE CHARACTERISTICS:
        ( A ) LENGTH: 30 base pairs
        ( B ) TYPE: nucleic acid
        ( C ) STRANDEDNESS: single
        ( D ) TOPOLOGY: linear ( i i ) MOLECULE TYPE: cDNA ( i i i ) HYPOTHETICAL: NO ( i i i ) ANTI-SENSE: NO ( v i ) ORIGINAL SOURCE:
        ( A ) ORGANISM: Mycobacterium avium ( x i ) SEQUENCE DESCRIPTION: SEQ ID NO: 41:

TGCTCTGTAG CAATGCGATG CGCGGATCGA 30

( 2 ) INFORMATION FOR SEQ ID NO: 42:

( i ) SEQUENCE CHARACTERISTICS:
        ( A ) LENGTH: 30 base pairs
        ( B ) TYPE: nucleic acid
        ( C ) STRANDEDNESS: single
        ( D ) TOPOLOGY: linear ( i i ) MOLECULE TYPE: cDNA (i i i) HYPOTHETICAL: NO (i i i) ANTI-SENSE: NO (v i) ORIGINAL SOURCE:
  (A) ORGANISM: Mycobacterium avium (x i) SEQUENCE DESCRIPTION: SEQ ID NO: 42:

TCGTAGCAAT GCGATGCGCG GATCGACCGT        30

(2) INFORMATION FOR SEQ ID NO: 43:

(i) SEQUENCE CHARACTERISTICS:
    (A) LENGTH: 30 base pairs
    (B) TYPE: nucleic acid
    (C) STRANDEDNESS: single
    (D) TOPOLOGY: linear (i i) MOLECULE TYPE: cDNA (i i i) HYPOTHETICAL: NO (i i i) ANTI-SENSE: NO (v i) ORIGINAL SOURCE:
    (A) ORGANISM: Mycobacterium avium (x i) SEQUENCE DESCRIPTION: SEQ ID NO: 43:

GTAGCAATGC GATGCGCGGA TCGACCGTCG        30

(2) INFORMATION FOR SEQ ID NO: 44:

(i) SEQUENCE CHARACTERISTICS:
    (A) LENGTH: 30 base pairs
    (B) TYPE: nucleic acid
    (C) STRANDEDNESS: single
    (D) TOPOLOGY: linear (i i) MOLECULE TYPE: cDNA (i i i) HYPOTHETICAL: NO (i i i) ANTI-SENSE: NO (v i) ORIGINAL SOURCE:
    (A) ORGANISM: Mycobacterium avium (x i) SEQUENCE DESCRIPTION: SEQ ID NO: 44:

CCACCACATT GCGGGTGACG AGTTCGATCG        30

(2) INFORMATION FOR SEQ ID NO: 45:

(i) SEQUENCE CHARACTERISTICS:
    (A) LENGTH: 30 base pairs
    (B) TYPE: nucleic acid
    (C) STRANDEDNESS: single
    (D) TOPOLOGY: linear (i i) MOLECULE TYPE: cDNA (i i i) HYPOTHETICAL: NO (i i i) ANTI-SENSE: NO (v i) ORIGINAL SOURCE:
    (A) ORGANISM: Mycobacterium avium (x i) SEQUENCE DESCRIPTION: SEQ ID NO: 45:

TATGGCAGAC GAGGTTCGCG CATACGGTTC        30

(2) INFORMATION FOR SEQ ID NO: 46:

( i ) SEQUENCE CHARACTERISTICS:
  ( A ) LENGTH: 30 base pairs
  ( B ) TYPE: nucleic acid
  ( C ) STRANDEDNESS: single
  ( D ) TOPOLOGY: linear ( i i ) MOLECULE TYPE: cDNA ( i i i ) HYPOTHETICAL: NO ( i i i ) ANTI-SENSE: NO ( v i ) ORIGINAL SOURCE:
  ( A ) ORGANISM: Mycobacterium avium ( x i ) SEQUENCE DESCRIPTION: SEQ ID NO: 46:

TCCCCTGAAA GTCGGCTTGC TCAACGACTA 30

( 2 ) INFORMATION FOR SEQ ID NO: 47:

( i ) SEQUENCE CHARACTERISTICS:
  ( A ) LENGTH: 30 base pairs
  ( B ) TYPE: nucleic acid
  ( C ) STRANDEDNESS: single
  ( D ) TOPOLOGY: linear ( i i ) MOLECULE TYPE: cDNA ( i i i ) HYPOTHETICAL: NO ( i i i ) ANTI-SENSE: NO ( v i ) ORIGINAL SOURCE:
  ( A ) ORGANISM: Mycobacterium avium ( x i ) SEQUENCE DESCRIPTION: SEQ ID NO: 47:

CTATGGCAGA CGAGGTTCGC GCATACGGTT 30

( 2 ) INFORMATION FOR SEQ ID NO: 48:

( i ) SEQUENCE CHARACTERISTICS:
  ( A ) LENGTH: 30 base pairs
  ( B ) TYPE: nucleic acid
  ( C ) STRANDEDNESS: single
  ( D ) TOPOLOGY: linear ( i i ) MOLECULE TYPE: cDNA ( i i i ) HYPOTHETICAL: NO ( i i i ) ANTI-SENSE: NO ( v i ) ORIGINAL SOURCE:
  ( A ) ORGANISM: Mycobacterium avium ( x i ) SEQUENCE DESCRIPTION: SEQ ID NO: 48:

CCGCTATGGC AGACGAGGTT CGCGCATACG 30

( 2 ) INFORMATION FOR SEQ ID NO: 49:

( i ) SEQUENCE CHARACTERISTICS:
  ( A ) LENGTH: 30 base pairs
  ( B ) TYPE: nucleic acid
  ( C ) STRANDEDNESS: single
  ( D ) TOPOLOGY: linear ( i i ) MOLECULE TYPE: cDNA ( i i i ) HYPOTHETICAL: NO ( i i i ) ANTI-SENSE: NO ( v i ) ORIGINAL SOURCE:
  ( A ) ORGANISM: Mycobacterium avium ( x i ) SEQUENCE DESCRIPTION: SEQ ID NO: 49:

TGCCGCTATG GCAGACGAGG TTCGCGCATA 30

( 2 ) INFORMATION FOR SEQ ID NO: 50:

( i ) SEQUENCE CHARACTERISTICS:
        ( A ) LENGTH: 30 base pairs
        ( B ) TYPE: nucleic acid
        ( C ) STRANDEDNESS: single
        ( D ) TOPOLOGY: linear ( i i ) MOLECULE TYPE: cDNA ( i i i ) HYPOTHETICAL: NO ( i i i ) ANTI-SENSE: NO ( v i ) ORIGINAL SOURCE:
        ( A ) ORGANISM: Mycobacterium avium ( x i ) SEQUENCE DESCRIPTION: SEQ ID NO: 50:

CACCACATTG CGGGTGACGA GTTCGATCGG 30

( 2 ) INFORMATION FOR SEQ ID NO: 51:

( i ) SEQUENCE CHARACTERISTICS:
        ( A ) LENGTH: 30 base pairs
        ( B ) TYPE: nucleic acid
        ( C ) STRANDEDNESS: single
        ( D ) TOPOLOGY: linear ( i i ) MOLECULE TYPE: cDNA ( i i i ) HYPOTHETICAL: NO ( i i i ) ANTI-SENSE: NO ( v i ) ORIGINAL SOURCE:
        ( A ) ORGANISM: Mycobacterium avium ( x i ) SEQUENCE DESCRIPTION: SEQ ID NO: 51:

CTGTCGTTGT CGGTGTCGCC GGACGTCGAA 30

( 2 ) INFORMATION FOR SEQ ID NO: 52:

( i ) SEQUENCE CHARACTERISTICS:
        ( A ) LENGTH: 30 base pairs
        ( B ) TYPE: nucleic acid
        ( C ) STRANDEDNESS: single
        ( D ) TOPOLOGY: linear ( i i ) MOLECULE TYPE: cDNA ( i i i ) HYPOTHETICAL: NO ( i i i ) ANTI-SENSE: NO ( v i ) ORIGINAL SOURCE:
        ( A ) ORGANISM: Mycobacterium avium ( x i ) SEQUENCE DESCRIPTION: SEQ ID NO: 52:

GATTGACGGC GCGTGGGACT CCTGCGTCGA 30

( 2 ) INFORMATION FOR SEQ ID NO: 53:

( i ) SEQUENCE CHARACTERISTICS:
        ( A ) LENGTH: 30 base pairs
        ( B ) TYPE: nucleic acid
        ( C ) STRANDEDNESS: single
        ( D ) TOPOLOGY: linear ( i i ) MOLECULE TYPE: cDNA ( i i i ) HYPOTHETICAL: NO ( i i i ) ANTI-SENSE: NO ( v i ) ORIGINAL SOURCE:
    ( A ) ORGANISM: Mycobacterium avium ( x i ) SEQUENCE DESCRIPTION: SEQ ID NO: 53:

TGTCGTTGTC GGTGTCGCCG GACGTCGGAT 30

( 2 ) INFORMATION FOR SEQ ID NO: 54:

( i ) SEQUENCE CHARACTERISTICS:
        ( A ) LENGTH: 30 base pairs
        ( B ) TYPE: nucleic acid
        ( C ) STRANDEDNESS: single
        ( D ) TOPOLOGY: linear ( i i ) MOLECULE TYPE: cDNA ( i i i ) HYPOTHETICAL: NO ( i i i ) ANTI-SENSE: NO ( v i ) ORIGINAL SOURCE:
        ( A ) ORGANISM: Mycobacterium avium ( x i ) SEQUENCE DESCRIPTION: SEQ ID NO: 54:

GTCGGTGTCG CCGGACGTCG GATAGTCGTT 30

( 2 ) INFORMATION FOR SEQ ID NO: 55:

( i ) SEQUENCE CHARACTERISTICS:
        ( A ) LENGTH: 30 base pairs
        ( B ) TYPE: nucleic acid
        ( C ) STRANDEDNESS: single
        ( D ) TOPOLOGY: linear ( i i ) MOLECULE TYPE: cDNA ( i i i ) HYPOTHETICAL: NO ( i i i ) ANTI-SENSE: NO ( v i ) ORIGINAL SOURCE:
        ( A ) ORGANISM: Mycobacterium avium ( x i ) SEQUENCE DESCRIPTION: SEQ ID NO: 55:

GCCGACTTTC AGGGGAGCGA CCGAACCGTA 30

( 2 ) INFORMATION FOR SEQ ID NO: 56:

( i ) SEQUENCE CHARACTERISTICS:
        ( A ) LENGTH: 30 base pairs
        ( B ) TYPE: nucleic acid
        ( C ) STRANDEDNESS: single
        ( D ) TOPOLOGY: linear ( i i ) MOLECULE TYPE: cDNA ( i i i ) HYPOTHETICAL: NO ( i i i ) ANTI-SENSE: NO ( v i ) ORIGINAL SOURCE:
        ( A ) ORGANISM: Mycobacterium avium ( x i ) SEQUENCE DESCRIPTION: SEQ ID NO: 56:

AAGTGGCGCA GTGCGATCGT GCCGACATTA 30

(2) INFORMATION FOR SEQ ID NO: 57:

(i) SEQUENCE CHARACTERISTICS:
        (A) LENGTH: 30 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iii) ANTI-SENSE: NO (vi) ORIGINAL SOURCE:
        (A) ORGANISM: Mycobacterium avium (xi) SEQUENCE DESCRIPTION: SEQ ID NO: 57:

CCGACTTTCA GGGGAGCGAC CGAACCGTAT      30

(2) INFORMATION FOR SEQ ID NO: 58:

(i) SEQUENCE CHARACTERISTICS:
        (A) LENGTH: 30 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iii) ANTI-SENSE: NO (vi) ORIGINAL SOURCE:
        (A) ORGANISM: Mycobacterium avium (xi) SEQUENCE DESCRIPTION: SEQ ID NO: 58:

ACTTTCAGGG GAGCGACCGA ACCGTATGCG      30

(2) INFORMATION FOR SEQ ID NO: 59:

(i) SEQUENCE CHARACTERISTICS:
        (A) LENGTH: 30 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iii) ANTI-SENSE: NO (vi) ORIGINAL SOURCE:
        (A) ORGANISM: Mycobacterium avium (xi) SEQUENCE DESCRIPTION: SEQ ID NO: 59:

TTTCAGGGGA GCGACCGAA CCGTATGCGCG      30

(2) INFORMATION FOR SEQ ID NO: 60:

(i) SEQUENCE CHARACTERISTICS:
        (A) LENGTH: 30 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iii) ANTI-SENSE: NO ( v i ) ORIGINAL SOURCE:
      ( A ) ORGANISM: Mycobacterium avium ( x i ) SEQUENCE DESCRIPTION: SEQ ID NO: 60:

GGAGACGGAA TGAACGCTCA CATCGACGCA      30

( 2 ) INFORMATION FOR SEQ ID NO: 61:

( i ) SEQUENCE CHARACTERISTICS:
      ( A ) LENGTH: 30 base pairs
      ( B ) TYPE: nucleic acid
      ( C ) STRANDEDNESS: single
      ( D ) TOPOLOGY: linear ( i i ) MOLECULE TYPE: cDNA ( i i i ) HYPOTHETICAL: NO ( i i i ) ANTI-SENSE: NO ( v i ) ORIGINAL SOURCE:
      ( A ) ORGANISM: Mycobacterium avium ( x i ) SEQUENCE DESCRIPTION: SEQ ID NO: 61:

CGTTCCCTAC CGACCTTCTC CGGGCGATTA      30

( 2 ) INFORMATION FOR SEQ ID NO: 62:

( i ) SEQUENCE CHARACTERISTICS:
      ( A ) LENGTH: 30 base pairs
      ( B ) TYPE: nucleic acid
      ( C ) STRANDEDNESS: single
      ( D ) TOPOLOGY: linear ( i i ) MOLECULE TYPE: cDNA ( i i i ) HYPOTHETICAL: NO ( i i i ) ANTI-SENSE: NO ( v i ) ORIGINAL SOURCE:
      ( A ) ORGANISM: Mycobacterium avium ( x i ) SEQUENCE DESCRIPTION: SEQ ID NO: 62:

GGAGACGGAA TGAACGCTCA CATCGACGCA      30

( 2 ) INFORMATION FOR SEQ ID NO: 63:

( i ) SEQUENCE CHARACTERISTICS:
      ( A ) LENGTH: 20 base pairs
      ( B ) TYPE: nucleic acid
      ( C ) STRANDEDNESS: single
      ( D ) TOPOLOGY: linear ( i i ) MOLECULE TYPE: cDNA ( i i i ) HYPOTHETICAL: NO ( i i i ) ANTI-SENSE: NO ( v i ) ORIGINAL SOURCE:
      ( A ) ORGANISM: Mycobacterium avium ( x i ) SEQUENCE DESCRIPTION: SEQ ID NO: 63:

GGCCCGATGC GACGTCGAGA      20

( 2 ) INFORMATION FOR SEQ ID NO: 64:

( i ) SEQUENCE CHARACTERISTICS:
      ( A ) LENGTH: 20 base pairs
      ( B ) TYPE: nucleic acid
      ( C ) STRANDEDNESS: single (D) TOPOLOGY: linear (ii) MOLECULE TYPE: cDNA (iii) HYPOTHETICAL: NO (iii) ANTI-SENSE: NO (vi) ORIGINAL SOURCE:
            (A) ORGANISM: Mycobacterium avium (xi) SEQUENCE DESCRIPTION: SEQ ID NO: 64:

GCGCAACTGC GCTTCGTCGA                                              20

(2) INFORMATION FOR SEQ ID NO: 65:

(i) SEQUENCE CHARACTERISTICS:
            (A) LENGTH: 30 base pairs
            (B) TYPE: nucleic acid
            (C) STRANDEDNESS: single
            (D) TOPOLOGY: linear (ii) MOLECULE TYPE: cDNA (iii) HYPOTHETICAL: NO (iii) ANTI-SENSE: NO (vi) ORIGINAL SOURCE:
            (A) ORGANISM: Mycobacterium avium (xi) SEQUENCE DESCRIPTION: SEQ ID NO: 65:

GAACGCCCGT TGCTGGCCAT TCACGAGGAG                                   30

(2) INFORMATION FOR SEQ ID NO: 66:

(i) SEQUENCE CHARACTERISTICS:
            (A) LENGTH: 30 base pairs
            (B) TYPE: nucleic acid
            (C) STRANDEDNESS: single
            (D) TOPOLOGY: linear (ii) MOLECULE TYPE: cDNA (iii) HYPOTHETICAL: NO (iii) ANTI-SENSE: NO (vi) ORIGINAL SOURCE:
            (A) ORGANISM: Mycobacterium avium (xi) SEQUENCE DESCRIPTION: SEQ ID NO: 66:

GCGCAACACG GTCGGACAGG CCTTCCTCGA                                   30

NUCLEOTIDE SEQUENCES WHICH HYBRIDIZE SPECIFICALLY WITH BACTERIAL STRAINS OF THE MYCOBACTERIUM AVIUM-INTRACELLULARE COMPLEX

BACKGROUND OF THE INVENTION (i) Field of the Invention

The present invention relates to a nucleic sequence specific for the *Mycobacterium avium-intracellulare* complex, as well as particular fragments of this sequence, which are capable of acting as nucleic probes for the detection of a nucleic acid specific for strains belonging to the *Mycobacterium avium-intracellulare* complex or as nucleic primers in the amplification of DNA or RNA obtained from strains of the *Mycobacterium avium-intracellulare* complex in a biological sample.

The invention also relates to a method of detection of strains belonging to the *Mycobacterium avium-intracellulare* complex in a biological sample using nucleic acid fragments, as well as a kit for implementing this method.

(ii) Description of Related Art

The number of infections caused by opportunistic mycobacteria is increasing, partly because they are frequent in AIDS patients. According to bacteriological studies carried out over the past few years, the most important opportunistic bacteria are: *M. kansasii, M. xenopi, M. simiae* and especially mycobacteria belonging to the complex: *M. avium-intracellulare* (MAI complex). However, geographical variations exist in the incidence of the infection by these various opportunistic mycobacteria.

In a recent study carried out by the Laboratory of Bacteriology and Virology of the Pitié-Salpêtrière hospital group directed by Professor J. Grosset, it was shown that among the 709 AIDS patients whose blood was cultured (2460 samples) 63 (8.9%) had positive haemocultures with mycobacteria. On the other hand, 84.1% of the positive haemocultures contained *M. avium-intracellulare* and 11.1% *M. tuberculosis*.

*M. avium* and *M. intracellulare* are two phenotypically related species indiscernible by conventional identification, and are therefore grouped into an MAI complex. MAI complex for the purposes of the present invention is understood to mean the strains as defined by SAITO et al. (J. Clin. Microbiol., August 1990, 28, p. 1694–1697). This complex brings together human and animal pathogens. In man non-infected by the HIV viruses, the infections are especially located in the lungs in adults and in the ganglia in children. MAI infections are diagnosed in 50 to 90% of AIDS patients. The locations are, in this case, preferably in the digestive system and are disseminated. MAI is also a pathogen which is important in veterinary medicine, affecting poultry, bovine, caprine and ovine species and the like. The animal pathogens, *M. paratuberculosis* and *M. silvaticum*, were recently introduced into the nomenclature as subspecies of *M. avium* (Thorel et al., Int. J. Syst. Bactériol., 1990, 40, 254–260). It should also be noted that strains of *M. paratuberculosis* were isolated from patients suffering from Crohn's disease.

Using serology, 28 serotypes are recognised within MAI. Currently, serotypes 1 to 6, 8 to 11 and 21 are classified as *M. avium* and serotypes 7, 12 to 20 and 25 as *M. intracellulare*. An uncertainty remains as to the taxonomic position of serotypes 22 to 24 and 26 to 28. In man non-infected with the HIV viruses, the distribution of the serotypes is highly dispersed whereas in AIDS patients, only serotypes 1, 4, 8 and 9 are predominant (data of the National Centre of Reference for Mycobacteria). This distribution is similar to that observed in animals where serotypes 1, 2, 3, 4, 8 are preferably found. The French epidemiological situation for the *M. avium* strains isolated from AIDS patients is different from that observed in the United States or in Sweden. While in France serotype 8 is predominant, serotypes 4 or 6 are the ones found in these other two countries.

The serotypes (or serovars) mentioned in the present patent are as defined by P. J. Brennan et al. (Identification of A typical Mycobacteria by Thin-Layer Chromatography of Their Surface Antigens, Journal of Clinical Microbiology, Oct. 1978, p. 374–379.

Opportunistic mycobacteria pose numerous challenges to the microbiologist, the immunologist and the clinician. Indeed, unlike *M. tuberculosis* which has a homogeneous bacterial population, the strains of the *M. avium-intracellulare* complex are composed of cells which give various types of colonies on culture; a discrepancy was observed between the response of patients to antituberculous chemotherapy and the results of the antibiogram in vitro, calling into question the role of antibiograms (in any case, the MAI infections respond barely or poorly to various antibiotic and antitubercolous treatments or the like); mycobacteria are responsible for the non-specific sensitization to tuberculin and can also affect the immune response.

In the laboratory, the difficulty consists in isolating opportunistic mycobacteria from various samples and then in determining the species. The ubiquitous presence of opportunistic mycobacteria in the environment often renders the distinction between colonization and infection difficult. That is why it is important to refer to precise clinical and bacteriological criteria before deciding on the clinical significance of a mycobacterinm isolated from a sample. Consequently, it is essential to establish a cooperation of good quality between clinicians and bacteriologists and to have reliable and specific techniques for identifying opportunistic mycobacteria. It is evident that the mycobacterial species isolated and identified from pathological products are linked to the isolation techniques and to the schemes used nowadays for their identification. Bacteriologists know that the identification of opportunistic mycobacteria is made difficult by several elements: certain species are more or less sensitive to the decontamination techniques required before the culture, several species are isolated in primary culture only under certain conditions, finally, certain identification techniques based on phenotypic properties are not sufficiently reliable and can lead to a wrong identification. On the other hand, the taxonomic status of certain mycobacteria related to the MAI complex still remains uncertain and, in this case, the identification cannot be established.

Mycobacteria of the *M. avium-intracelllulare* complex can, like *M. tuberculosis*, be responsible for adenites in children. The clinician frequently gives an initial antituberculous treatment while awaiting the microbiological diagnosis which may take up to several weeks, this treatment being stopped as soon as the microbiological diagnosis is obtained.

In order to avoid these errors of interpretation and to permit a rapid diagnosis, the inventors responsible for the present invention set themselves the objective of isolating DNA sequences specific for mycobacteria belonging to the *M. avium-intracellulare* complex and of developing, using these sequences, a method of identification based on the PCR technique and the molecular hybridization technique. They therefore searched for sequences which can be used both for the diagnosis and for the molecular epidemiology.

Recently, approaches using molecular hybridization to identify *M. avium-intracellulare* species have been proposed; however, most of these methods permit identification only after culture since they are not sufficiently sensitive to detect these mycobacteria directly in the biological samples. This is the case for example for the cDNA probe which is complementary to ribosomal RNA sequences and marketed by Gene-Probe (San Diego, Calif.), see WO 84/02721, WO 88/03957, Musial, C. E. et al. (J. Clin. Microbiol., 1988, 26, 2120–2123). Furthermore, mycobacterial strains according to the criteria of Saito et al. (J. Clin. Microbiol, 1990, 28, 1694–1697) are not detectable using the probes marketed by Gene-Probe. Other authors have found similar results: Enns, R. K. (Lab. Med. 1988, 19, 295–300), Sherman, I. et al. (J. Clin. Microbiol., 1989, 27, 241–244).

FR-2,645,878 describes, in addition, a nucleic sequence of 383 base pairs homologous in at least 5 mycobacteria species including *M. tuberculosis*.

This sequence has, however, the disadvantage of not being specific for the *M. avium-intracellulare* complex.

A more sensitive and more specific method was therefore necessary in order to establish a reliable diagnosis for atypical mycobacterioses and a precise identification of the various opportunistic mycobacteria.

SUMMARY OF THE INVENTION

The object of the present invention is to provide such a method as well as the elements using this method.

The subject of the present invention is thus a nucleic acid sequence which hybridizes specifically with a genomic nucleic acid sequence of the strains belonging to the *Mycobacterium avium-intracellulare* complex, chosen from the nucleotide sequence SEQ ID No. 1, the nucleotide sequence SEQ ID No. 2, sequences complementary to these, as well as the sequences differing therefrom by mutation, insertion, deletion or substitution of one or more bases, and which does not hybridize with the nucleic acids of mycobacteria not belonging to the said complex.

The subject of the present invention is also a nucleic acid sequence chosen from the nucleotide sequences SEQ ID No. 1 and SEQ ID No. 2, their complementary sequences as well as the sequences differing therefrom by mutation, insertion, deletion or substitution of one or more bases and which have the same specificity.

The nucleic acid sequences defined above can be DNA sequences or RNA sequences.

The exact size of the fragment of sequence SEQ ID No. 2 (fragment I6) is 1642 base pairs. The search in the EMBL and Genbank data banks revealed no significant homology with the DNA sequences already known. Fragment I6 was cloned into the plasmid pUC18 and the recombinant plasmid is called pMA01.

The plasmid pMA01 was deposited at the Collection nationals de Cultures de Microorganismes on 28 Aug. 1991 under the no. 1-1137.

The fragment of sequence SEQ ID No. 1 (fragment I1) used as probe on the different *M. avium-intracellulare* serotypes shows a hybridization with serotypes 2, 3, 7, 12, 13, 14, 15, 16, 17, 18, 19, 20, 23, 24 and 25. Fragment I1 (SEQ ID No. 1) hybridizes with *M. intra-cellulare* strains and the *M. avium* strains serotypes 2 and 3.

Nowadays, serovars 1, 2, 3, 4, 5, 6, 8, 9, 10, 11 and 21 are considered as *M. avium* and serovars 7, 12, 13, 14, 15, 16, 17, 18, 19, 20 and 25 as *M. intracellulare*.

Fragment I1 (SEQ ID No. 1), whose size is equal to 2004 base pairs, has been cloned into the plasmid pUC18; the recombinant plasmid is called pMA02.

The plasmid pMA02 was deposited at the Collection Nationals de Cultures de Microorganismes on 28 Aug. 1991 under the no. 1-1138.

These plasmids, as well as, more generally, a cloning vector containing a nucleic acid sequence as defined earlier, constitute another subject of the invention.

An examination of the data bank reveals no homology between the sequence of I1 (SEQ ID No. 1) and known sequences.

Fragments I6 (SEQ ID No. 2) and I1 (SEQ ID No. 1), functionally equivalent portions or variants thereof, can be used in molecular hybridization techniques for the detection and identification of species of the *M. avium-intracellulare* complex. The functionally equivalent variants comprise sequences in which base pairs have been mutated, deleted, inserted or substituted without the properties essential for the specificity of these fragments being affected.

A nucleic acid fragment of 700 base pairs obtained by cleaving the initial fragment I6 (SEQ ID No. 2) with the restriction enzymes SalI and EcoRI was used as probe on the DNA of the different serotpyes of *M. avium*. A hybridization is observed only with the DNA of the *M. avium* strains carrying the serotypes 1, 2, 3, 4, 5, 6, 8, 9, 10, 11 and 21. It is important to note that this 700 base pair probe makes it possible to detect the *M. avium* serotypes most often encountered in AIDS patients.

The sequences I6 (SEQ ID No. 2) and I1 (SEQ ID No. 1) or the fragments obtained from these sequences can also be used to select primers for the PCR technique.

This technique necessitates the choice of oligonucleotide pairs flanking the fragment which should be amplified (U.S. Pat. No. 4,683,202). These oligodeoxyribonucleotide or oligoribonucleotide primers have advantageously a length of between 18 and 30 and preferably 18 and 22 nucleotides. One of the two primers is complementary to the (+) strand of the template and the other primer is complementary to the (−) strand. It is important that these primers do not possess a secondary structure or a mutually complementary sequence. On the other hand, the length and the sequence of each primer should be chosen such that the primers do not hybridize with other nucleic acids obtained from prokaryotic or eukaryotic cells, in particular with the nucleic acids of mycobacteria not belonging to the *M. avium-intracellulare* complex and with human DNA or RNA which may possibly contaminate the sample.

The amplimers selected as specific primers for the amplification of nucleic sequences of strains belonging to the MAI complex were chosen according to the method described by Griffais et al. (Nucleic Acids Res. 1991, 19, 3887–3891).

From sequence I6 (SEQ ID No. 2), the inventors chose oligonucleotides in order to perform a PCR test. Using these oligonucleotides, they obtained an amplification specific for *M. avium* (serotypes 1, 2, 3, 4, 5, 6, 8, 9, 10, 11 and 21) and for *M. paratuberculosis*, no amplifcation was visible with a nucleic acid of *M. scrofulaceum*, or of mcycobacteria belonging to the tuberculosis complex.

Likewise, from sequence I1 (SEQ ID No. 1), the inventors selected oligonucleotide primers which made it possible to develop a specific PCR test. With the primers selected from fragment I1 (SEQ ID No. 1), they observed a fragment amplified only when the nucleic acid subjected to amplification came from the *M. avium-intracellulare* strains carrying serotypes 2, 3, 7, 12, 13, 14, 15, 16, 17, 18, 19, 20, 23, 24 and 25.

The preferred pairs of primers are represented in FIG. 1. The oligonucleotide pairs which can be used as primers comprise preferably at least 18 consecutive nucleotides chosen while conserving the 3' end of the sequences.

The most particularly preferred pair of primers are represented by the pairs consisting of oligonucleotides MA1 and MA2 derived from sequence I6 (SEQ ID No. 2) on the one hand, and MA3 and MA4 derived from sequence I1 (SEQ ID No. 1) on the other hand, of sequences: [SEQ ID NOS: 63–66]

```
MA1:  5'GGC CCG ATG CGA CGT CGA GA3'
MA2:  5'GCG CAA CTG CGC TTC GTC GA3'
MA3:  5'GAA CGC CCG TTG CTG GCC ATT CAC GAG GAG3'
MA4:  5'GCG CAA CAC GGT CGG ACA GGC CTT CCT CGA3'
```

The amplified fragments can be identified after an agarose or polyacrylamide gel electrophoresis or after a capillary electrophoresis or alternatively after a chromatographic technique (gel filtration, hydrophobic or ion-exchange chromatography). The specificity of the amplification can be controlled by molecular hybridization using, as probes, the nucleic sequences I6 (SEQ ID No. 2) or I1 (SEQ ID No. 1), fragments thereof, plasmids containing these sequences or fragments thereof, oligonucleotides complementary to these sequences or fragments of sequences or products of amplification. These probes can be labelled or otherwise with radioactive elements or with non-radioactive molecules.

These probes comprise advantageously at least 20 consecutive nucleotides among the sequences or fragments of sequences mentioned above, and constitute another subject of the invention.

The probes are DNA probes or RNA probes.

The nucleic acid sequences described in this invention can thus be used as probes to detect specifically and directly strains belonging to the *M. avium-intracellulare* complex in a biological sample. The non-labelled sequences can be used directly as probes, however, the nucleic acid sequences are generally labelled with a radioactive element ($^{32}$P, $^{35}$S, $^{3}$H, $^{125}$I) or with a non-radioactive molecule (biotin, acetylaminofluorene, digoxygenin, 5-bromodeoxyuridine) in order to obtain probes which can be used for numerous applications.

In this latter case, one of the labelling methods described in FR 2,422, 956 and FR 2,518,755 can be used. The hybridization technique can be carried out in various ways (Matthews, J. A. and Kricka, L. J., Anal. Biochem. 1988, 169, 1–25). The method most widely used consists in immobilizing the nucleic acid extracted from the mycobacterial cells on a support (nitrocellulose, nylon, polystyrene and the like) and in incubating, under well defined conditions, the immobilized target nucleic acid with the probe nucleic acid. After hybridization, the excess probe is removed and the hybrid molecules formed are detected by the appropriate method (measurement of the radioactivity, the fluorescence or the enzymatic activity linked to the probe and the like).

In another application, the nucleic acid probes described here can be used as capture probes. In this process, the probe is immobilized on a support and is used to capture by specific hybridization the target nucleic acid extracted from the mycobacteria. If necessary, the solid support is separated from the sample and the duplex formed between the capture probe and the target nucleic acid is then detected by means of a second detection probe labelled with an easily detectable element.

When a sufficient quantity of mycobacterial nucleic acid can be extracted from the samples to be analysed, the sequences described in the patent can be used to detect and identify the strains belonging to the *M. avium-intracellulare* complex directly in these samples. In the opposite case, a rapid culture in liquid medium can be carried out before extraction of the mycobacterial nucleic acid or, alternatively, the small quantity of mycobacterial nucleic acid extracted from the sample can be subjected to the PCR technique.

The subject of the present invention is also a method of detection of the presence of strains belonging to the *Mycobacterium avium-intracellulare* complex in a biological sample, characterized by the following steps:

i) bringing the biological sample into contact with a pair of nucleic acid fragments, called primers, as defined earlier, the nucleic acid contained in the sample having been, where appropriate, previously rendered accessible to hybridization and under conditions permitting a hybridization of the primers to the nucleic acid of the strains belonging to the *Mycobacterium avium-intracellulare* complex;

ii) amplification of the nucleic acid of the strains belonging to the *Mycobacterium avium-intracellulare* complex;

iii) visualization of the amplification of nucleic acid fragments corresponding to the fragment flanked by the primers;

iv) optional verification of the sequence of the amplified fragment, for example by specific probe hybridization, by sequencing or by restriction site analysis.

The subject of the present invention is, in addition, a kit for the detection of the presence of strains belonging to the *Mycobacterium avium-intracellulare* complex in a biological sample, characterized in that it comprises the following elements:

a pair of nucleic acid fragments as defined earlier;

the reagents necessary for carrying out an amplification of nucleic acid of strains belonging to the *Mycobacterium avium-intracellulare* complex;

optionally a component which makes it possible to verify the sequence of the amplified fragment, more particularly a nucleic probe as defined earlier.

This kit more advantageously contains the labelled or non-labelled probe(s). These can be in solution or immobilized on a support. The kit may also contain the reagents necessary for lysis of the mycobacteria and extraction of the target nucleic acids, as well as the hybridization and washing solutions corresponding to the chosen method.

The invention is illustrated in greater detail in the following description, for which reference should be made to the accompanying figures in which:

BRIEF DESCRIPTION OF THE DRAWINGS

FIG. 1 represents the nucleotide sequences suitable for the choice of oligonucleotide primers.

*M. avium* (A), *M. intracellulare* (B), *M. tuberculosis* (C). The arrow indicates the relevant fragment of 1642 base pairs.

Figures 3A, 3B, 3C:
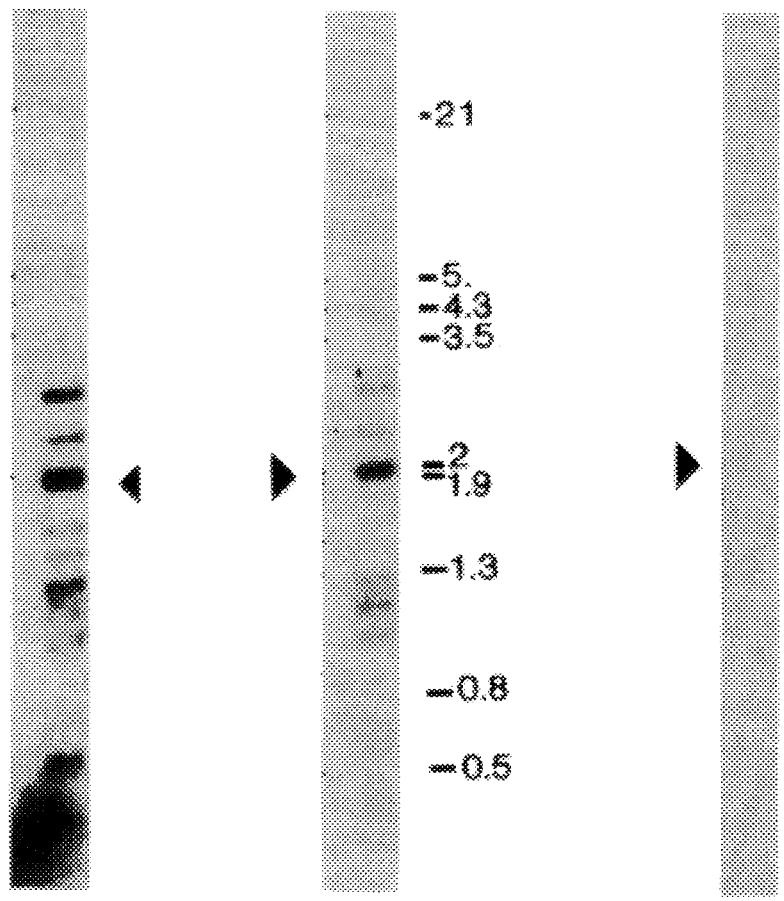

FIGS. 3A, 3B and 3C represent the Southern blot analysis of the cosmid DNA I1 SEQ ID No. 1.

15 µl of cosmid DNA approximately corresponding to 3 µg were digested with 10 units of enzyme SalI. After electrophoresis, the DNA was transferred onto nitrocellulose and hybridized with the radioactive probes: M. avium (A), M. intracellulare (B), M. tuberculosis (C). The arrow indicates the relevant fragment of 2004 base pairs.

Figure 4A:
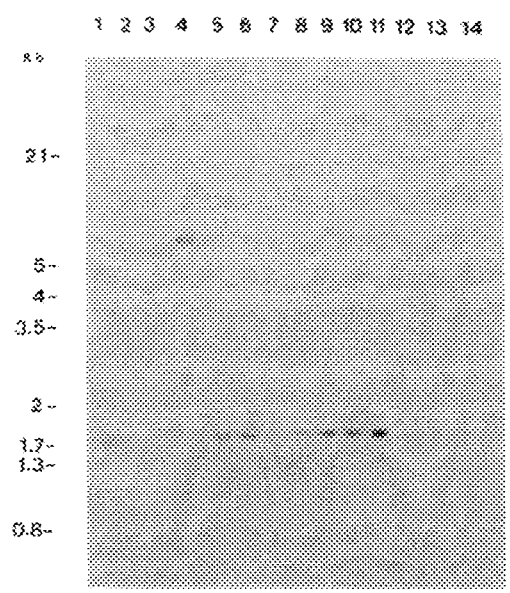
Figure 4B:
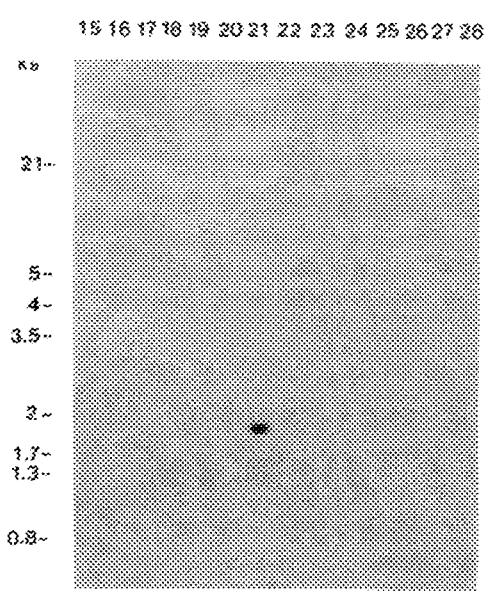

FIG. 4 represents the Southern blot analysis of the DNA of mycobacteria of the M. avium-intracellulare complex.

2 µg of DNA were digested with 10 units of enzyme PstI. After electrophoresis, the DNA was transferred onto nitrocellulose and hybridized with 25 ng of the radio-labelled SalI-EcoRI fragment derived from I6 SEQ ID No. 2. This probe detects fragments in serotypes 1, 2, 3, 4, 5, 6, 8, 9, 10, 11 and 21.

Figure 5A:
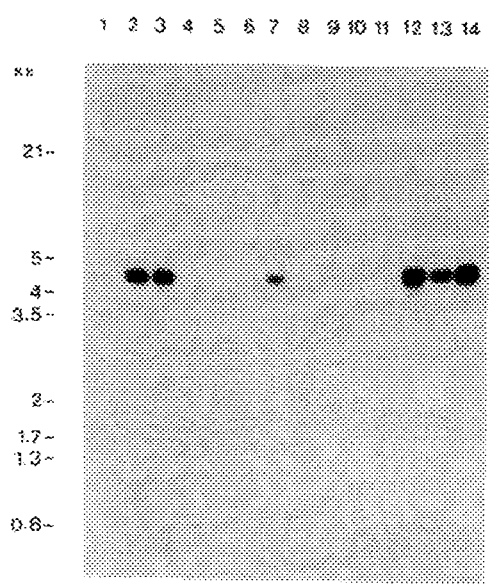
Figure 5B:
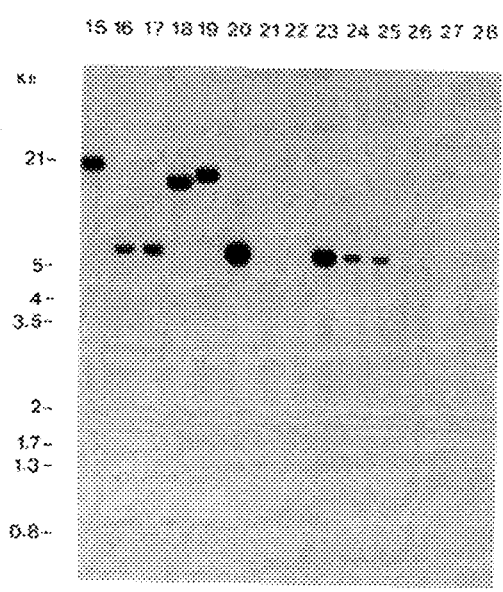

FIG. 5 represents the Southern blot analysis of the DNA of mycobacteria of the M. avium-intracellulare complex.

2 µg of DNA were digested with 10 units of enzyme PstI. After electrophoresis, the DNA was transferred onto nitrocellulose and hybridized with 25 ng of the radio-labelled SalI-BamHI fragment derived from I1 SEQ ID No. 1. This probe detects fragments in serotypes 2, 3, 7, 12, 13, 14, 15, 16, 17, 18, 19, 20, 23, 24 and 25.

Figure 6A:
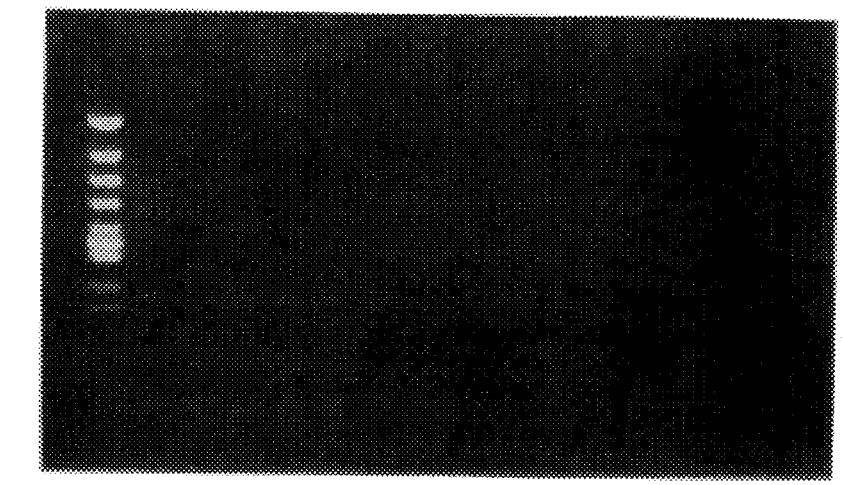
Figure 6B:
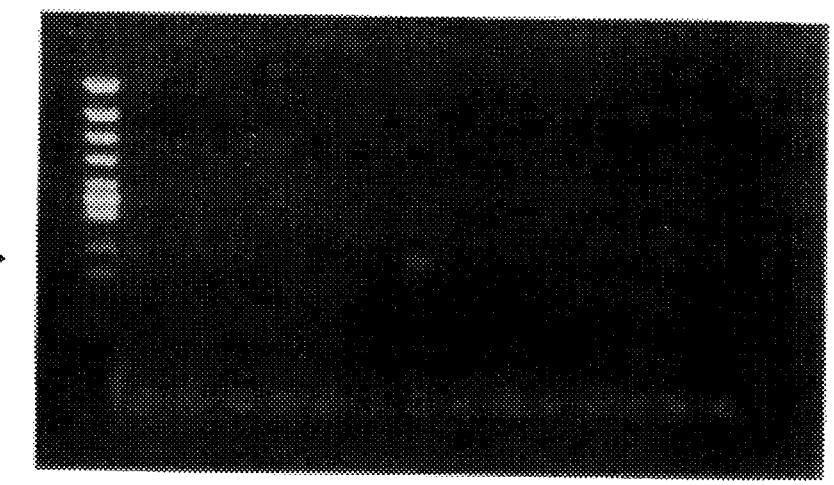

FIG. 6 represents the agarose gel analysis of the amplified samples.

10 µl of the samples amplified with the pair of primers No. 1 described in FIG. 1 and derived from the fragment I6 (SEQ ID No. 2) are deposited on a 2% agarose gel in TAE. The amplified fragments corresponding to serotypes 1, 2, 3, 4, 5, 6, 8, 9, 10, 11 and 21 are visualized under UV in the presence of ethidium bromide.

Figure 7A:
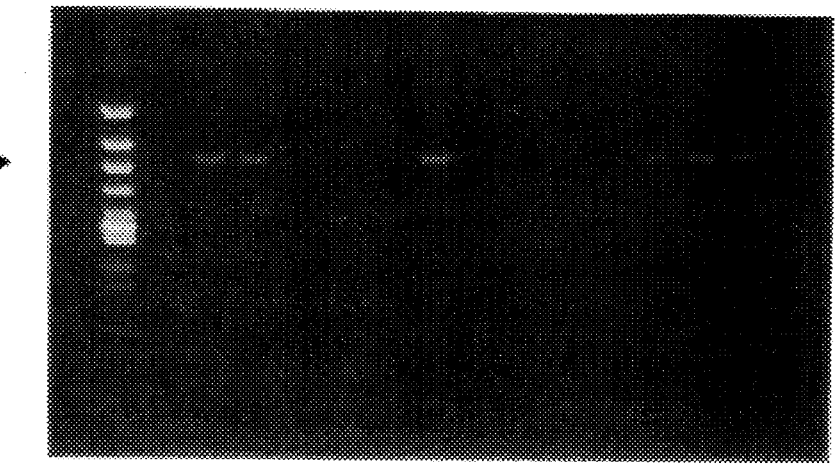
Figure 7B:
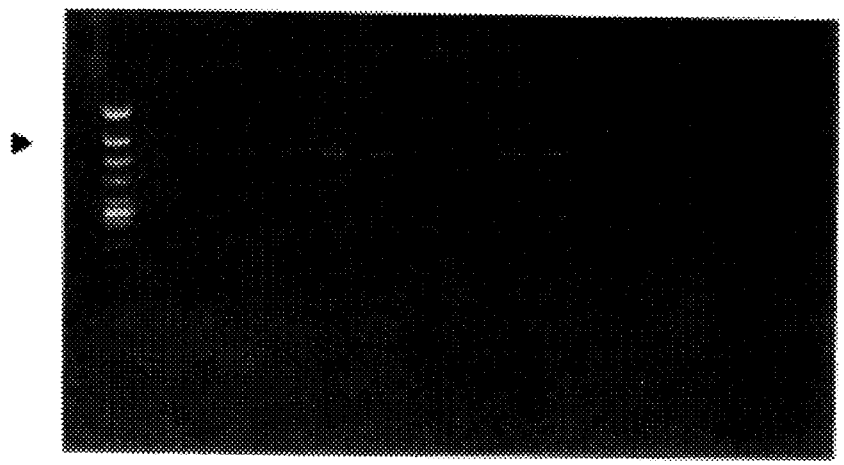

FIG. 7 represents the agarose gel analysis of the amplified samples.

10 µl of the samples amplified with the oligonucleotides MA3 and MA4 derived from the fragment I1 SEQ ID No. 1 are deposited on a 2% agarose gel in TAE. The amplified fragments corresponding to serotypes 2, 3, 7, 12, 13, 14, 15, 16, 17, 18, 19, 20, 23, 24 and 25 are visualized under UV in the presence of ethidium bromide.

Figure 8A:
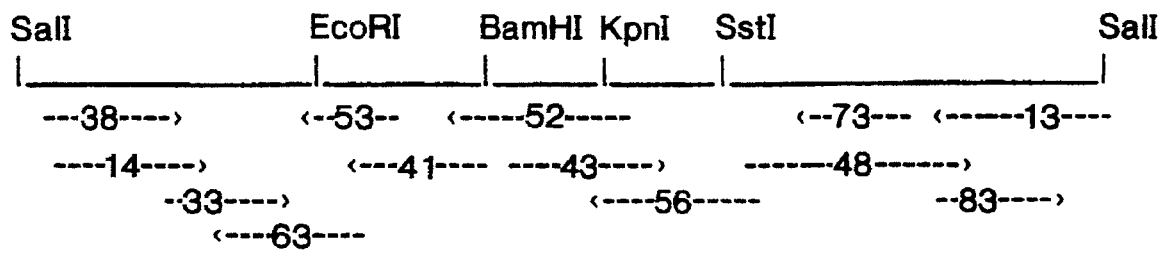
Figure 8B:
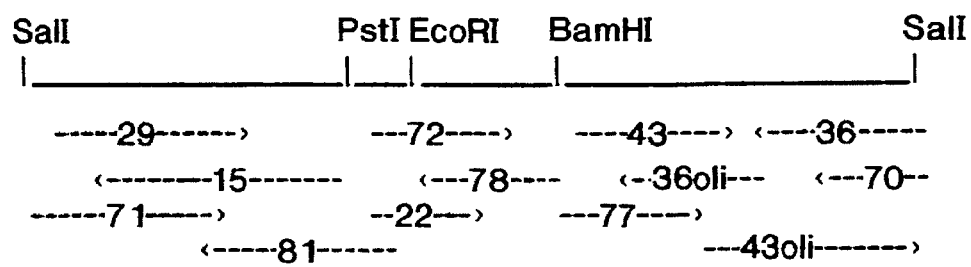

FIGS. 8A and 8B represent the diagrams of the strategies followed for sequencing the fragments I6(A) SEQ ID No. 2 and I1 (SEQ ID No. 1) (B).

DETAILED DESCRIPTION OF PREFERRED EMBODIMENTS

Construction of the M. avium Genomic Library

Screening of the Library and Determination of the Sequence of the Specific Fragments The genomic DNA of M. avium (serotype 2) is partially digested with the restriction endonuclease SalI by reacting 0.03 U of enzyme per µg of DNA in the buffer recommended by the supplier, for 1 hour at 37° C. The genomic DNA thus digested is separated by electrophoresis on 0.4% agarose gel. The fragments whose length is between 30 and 40 kb are electroeluted and precipitated with ethanol after phenol/chloroform (1/1) extractions.

The vector is the cosmid pHC79. It is digested in the same manner and dephosphorylated in order to avoid any self-ligation.

The ligation is carried out by mixing 700 ng of vector, 0.8 µg of DNA fragments of 30/40 kb, the mixture is left at 14° C. for 18 h after having added 2.5 units of T4 DNA ligase in an appropriate buffer.

The recombinant cosmids are packaged in vitro and used to transform the bacteria (HB101). The transformed bacteria are incubated for 1 h at 37° C. in LB medium and then plated on selective agar medium containing 25 µg/ml of ampicillin. The ampicillin-resistant colonies are all tested for their sensitivity to tetracycline, the DNA fragment of 30/40 kb having been inserted into the vector so as to inactivate the tetracycline resistance gene (Tet) and to conserve the ampicillin resistance gene (Amp).

A mini-preparation of DNA from the first 80 transformant colonies resistant to ampicillin (Amp$^r$) and sensitive to tetracycline (Tet$^s$) is performed according to the alkaline lysis technique. The DNA from these preparations is than digested with the restriction endonuclease SalI, analysed by electrophoresis on 0.8% agarose gel and then transferred onto nylon filters. The DNA is irreversibly bound by exposure for 5 min to UV at 254 nm.

These different filters are incubated for 16–18 hours at 68° C. in 6× SSC buffer (1× SSC corresponds to 0.15M NaCl and 0.015M Na citrate) containing 10% dextran sulphate, a 5× concentrated Denhardt solution (a 1× Denhardt solution corresponds to 0.02% Ficoll, 0.02% polyvinylpyrrolidone and 0.02% bovine serum albumin), 10 mM EDTA, 0.5% SDS, 100 µg/ml of denatured salmon sperm DNA and genomic DNA radiolabelled with $^{32}$phosphorus by multipriming, of one of the following three species: M. avium, M. intracellulare, M. tuberculosis H37rv.

After hybridization, the filters are washed twice for 10 min in 2× SSC at 65° C., once for 30 min in 2× SSC supplemented with 0.1% SDS at 65° C. and finally once for 10 min in 0.1× SSC at 65° C. The filters, still moist, are subjected to autoradiography at −80° C. with an intensifying screen for 1 h to 2 days.

The results of these hybridizations made it possible to isolate two cosmid clones containing fragments of about 2 kb, called I6 SEQ ID No. 2 and I1 (SEQ ID No. 1).

Figures 2A, 2B, 2C:
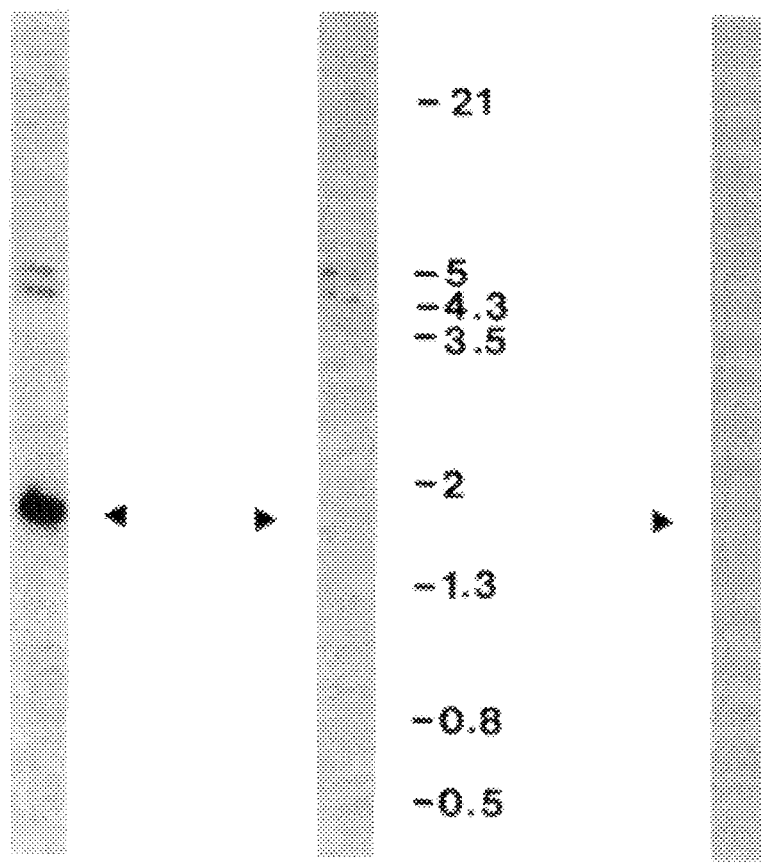
FIGS. 2A, 2B and 2C represent the Southern blot analysis of the cosmid DNA I6 (SEQ ID No. 2) of cosmid DNA, 15 μl of DNA approximately corresponding to 3 μg were digested with 10 units of enzyme SalI. After electrophoresis, the DNA was transferred onto nitrocellulose and hybridized with the radioactive probes.

Fragment I6 hybridizes only with the genomic DNA of M. avium, fragment I1 SEQ ID No. 1 hybridizes with the DNA of M. avium and M. intracellulare. Neither hybridizes with the labelled DNA of M. tuberculosis H37rv (FIGS. 2 and 3).

Fragments I6 SEQ ID No. 2 and I1 SEQ ID No. 1 were cloned into a vector pUC18 and prepared in large quantities. The resulting plasmids were called pMA01 and pMA02 respectively.

These fragments were cleaved by the enzymes SmaI, BamHI, PstI and EcoRI, and then cloned into the phages M13mp18 and M13mp19 and sequenced according to the Sanger method using Taq polymerase in the presence of d-azaGTP in place of dGTP. All the sequencing reactions were carried out with $^{35}$S-labelled dATP.

The diagrams of FIG. 8 represent the strategies followed for the sequencing of fragments I6 SEQ ID No. 2 and I1 SEQ ID No. 1.

The entire sequences of the fragments are represented in the appendix (SEQ ID No. 2 and SEQ ID No. 1 corresponding to fragment I6 SEQ ID No. 2 and fragment I1 SEQ ID No. 1 respectively). The composition between the whole of the Los Alamos data bank and the 1642 nucleotides of fragment I6 SEQ ID No. 2 and the 2004 nucleotides of fragment I1 SEQ ID No. 1, thus determined, reveal no significant homology with the sequences currently known.

The invention is illustrated by the following examples:

EXAMPLE 1

Analysis of mycobacterial DNA by the Southern technique using, as probes, the nucleic acid sequences of the invention.

The list of mycobacteria used in this study is given in the following table:

TABLE

Names of the strains used

| SPECIES | STRAIN | CIPT* REFERENCE |
|---|---|---|
| M. avium | ATCC** 25291 | 031 002 |
| subsp. paratuberculosis | ATCC 19698 | 112 0001 |
| M. intracellulare | ATCC 13950 | 031 0001 |
| M. scrofulaceum | ATCC 19981 | 022 0001 |
| M. tuberculosis | ATCC 27294 | 001 0001 |
| M. bovis | ATCC 19210 | 002 0001 |
| M. bovis BCG Pasteur | TMC*** 1011 | 004 0004 |

*Collection Institut Pasteur Tuberculose
**American Type Culture Collection
***Trudeau Mycobacterial Collection After culture on Lowenstein-Jensen or Middlebrook 7H9 media, the mycobacteria are lysed using the following technique: the bacteria are centrifuged for 30 minutes at 7000 g, resuspended in 20 ml of 7H9 medium containing 100 µg/ml of D-cycloserine, 14 µg/ml of glycine, 200 µg/ml of lysozyme and 6 mM of EDTA and then incubated at 37° C. for 18 hours in 4 ml of lysis buffer consisting of 50 mM Tris-HCl, pH 8, 50 mM EDTA, 100 mM NaCl, 0.5% SDS and containing 60 µg/ml of pronase.

After the lysis, the DNAs are extracted with phenol-chloroform mixture and precipitated with ethanol. The DNAs thus extracted are subjected to a total digestion with the enzyme PstI. The fragments obtained are then separated by electrophoresis on a 0.8% agarose gel in TAE before being transferred onto nitrocellulose membrane according to the Southern technique.

The fragments transferred are analysed by molecular hybridization. In this example, the probes used are the fragment of 700 base pairs extracted by digestion of fragment I6 SEQ ID No. 2 with the enzymes SalI and EcoRI and pMA02 which are labelled with $^{32}$phosphorus according to the technique of the "Multiprime" kit marketed by Amersham. The results are presented in FIGS. 4 and 5.

The probe derived from sequence I6 SEQ ID No. 2 detects two fragments with the DNAs of the M. avium strains (serotypes 1, 2, 3, 5, 6, 8, 9, 10, 11 and 21) and only one fragment with the DNAs of the strain carrying serotype 4. The size of these fragments varies with the strain tested, different patterns are thus obtained by Southern blotting (FIG. 4).

The probe pMA02, containing sequence I1 SEQ ID No. 2, detects a single fragment on the DNAs of the M. avium-intracellulare strains (serotypes 2, 3, 7, 12, 13, 14, 15, 16, 17, 18, 19, 20, 23, 24 and 25). The size of the fragment obtained is variable and is between about 5 and 20 kb (FIG. 5).

EXAMPLE 2

Enzymatic amplification in vitro of the DNA of M. avium-intracellulare strains with the primers defined from the nucleic acid sequences which are the subject of the invention.

Synthesis of the Oligonucleotide Primers

The primers derived from sequences I6 SEQ ID No. 2 and I1 SEQ ID No. 1 and having a length of between 18 and 22 nucleotides were synthesized in an Applied Biosystem automated apparatus based on the chemistry of phosphoramidites. After the synthesis, the oligonucleotide solution is transferred into a glass tube and incubated with concentrated ammonium hydroxide at 50° C. for 4 hours. The ammonium hydroxide is then evaporated in a Speed Vac/Concentrator and the pellet is washed twice with sterile distilled water and dried. Finally, the pellet is taken up in 0.5 ml of Tris-HCl buffer, pH 8.0 containing 1 mM EDTA. The concentration of each primer is determined using a spectrophotomer and an aliquot is analysed by electrophoresis on a polyacrylamide gel in order to verify that the primer is not degraded.

Isolation of the Mycobacterial DNA

The biological extracts are treated in an appropriate manner and then centrifuged. The DNA is extracted by resuspending the pellet with 50 µl of 0.1M NaOH containing 2M NaCl and 0.5% SDS. The mixture is incubated at 95° C. for 15 minutes; 400 µl of 0.1M Tris-HCl, pH 7, are added to the reaction mixture. The DNA is extracted 3 times with phenol/chloroform, precipitated with ethanol and taken up in 50 µl of 10 mM Tris buffer, pH 8, containing 0.1 mM EDTA.

Amplification

The enzymatic amplification technique in vitro (PCR) is carried out according to the procedure described by Saiki et al. (Science, 1988, 239, 487–491) using 12.5 pmol of the oligonucleotides of the pair of primers No. 1 of FIG. 1, on the one hand, or MA3 and MA4, on the other hand, and 5 ng of DNA of different strains of mycobacteria with 2 units of Taq polymerase in a buffer containing 50 mM KCl, 10 mM Tris-HCl, pH 8.3, 2 mM MgCl$_2$, 300 µM of deoxyribonucleotide triphosphates and 100 µg/ml of gelatin, the final volume of the reaction being 100 µl. The parameters for the PCR stages were chosen in the following manner: 2 min at 94° C., 2 min at 50° C., 2 min at 72° C. Thirty cycles are carried out using an automated apparatus. After the last cycle, the samples are maintained at 4° C. until the analysis.

Electrophoretic Analysis on an Agarose Gel of the Amplified Samples

Ten µl of the samples are loaded onto a 2% agarose gel in a TAE buffer (0.04M Tris-acetate, 0.001M EDTA) containing 1 µg/ml of ethidium bromide. The amplified fragments are visualized under UV and the gels are photographed using a Polaroid 667 film.

FIGS. 6 and 7 show the results obtained with different mycobacteria DNAs and the pair of primers No. 1, on the one hand (FIG. 6), and with the primers MA3 and MA4 on the other hand (FIG. 7).

When the pair of primers No. 1 is used, a DNA fragment corresponding to the expected size is observed with the DNAs of the following mycobacteria: M. avium (serotypes 1, 2, 3, 4, 5, 6, 8, 9, 10, 11 and 21) and M. paratuberculosis.

It is important to note that the pair of primers No. 1 makes it possible to detect M. paratuberculosis, making the method usable in the field of veterinary medicine. Indeed, M. paratuberculosis is responsible for Johne's disease in ruminants. This diseases poses an economic threat; it results in a loss of production of meat and milk of which the cost is estimated, in the United States of America, at one billion dollars per year.

When the pair of primers MA3 and MA4 is used, a DNA fragment corresponding to the expected size is observed with the DNAs of the following mycobacteria: M. avium (serotypes 2, 3, 7, 12, 13, 14, 15, 16, 17, 18, 19, 20, 23, 24 and 25).

On the other hand, no amplified fragment is visible when the DNA analysed is extracted from the following strains: M. tuberculosis, M. boris, M. bovis-BCG, M. microti, M. scrofulaceum, M. fortuitum, M. kansasii and when one of the pairs of primers No. 1, the pair MA1 and MA2 or the pair MA3 and MA4 is used to direct the amplification.

We claim:

1. A purified nucleic acid sequence selected from the group consisting of the nucleotide sequence SEQ ID No. 1, the nucleotide sequence SEQ ID No. 2, sequences complementary to the nucleotide sequences of SEQ ID No. 1 or SEQ ID No. 2, and fragments of SEQ ID No. 1 or SEQ ID No. 2 which specifically hybridize to only a genomic nucleic acid sequence of the *Mycobacterium avium-intracellulare* complex.

2. A purified nucleic acid sequence which hybridizes specifically to only a genomic nucleic acid of the serotypes 2, 3, 12, 13, 14, 15, 16, 17, 18, 19, 20, 23, 24 and 25, of the *M. avium-intracellulare* complex comprising the nucleotide sequence SEQ ID No. 1, a sequence complementary thereto, and fragments thereof which specifically hybridize to only a genomic nucleic acid sequence of the serotypes 2, 3, 12, 13, 14, 15, 16, 17, 18, 19, 20, 23, 24, and 25 of the *Mycobacterium avium-intracellulare* complex.

3. A purified nucleic acid sequence which hybridizes specifically with only a genomic nucleic acid sequence of the *M. avium* serotypes 1, 2, 3, 4, 5, 6, 8, 9, 10, 11, or 21, said nucleic acid sequence comprising a nucleic acid fragment of 700 base pairs which is obtained by cleaving a nucleic acid having the nucleotide sequence SEQ ID No. 2 with SalI and EcoRI.

4. An oligonucleotide primer pair specific for the amplification of a nucleic sequence of the strains belonging to the *Mycobacterium avium-intracellulare* complex, comprising a pair of oligonucleotides having 18 to 30 nucleotides whose sequences are selected from the group consisting of the sequences according to claim 1.

5. An oligonucleotide primer pair according to claim 4 comprising a pair of oligonucleotides having 18 to 22 nucleotides.

6. An oligonucleotide primer pair selected from the group consisting of the oligonucleotide pair MA1 and MA2 having the sequences:

MA1: 5'GGC CCG ATG CGA CGT CGA GA3' SEQ ID No. 63 and
MA2: 5'GCG CAA CTG CGC TTC GTC GA3' SEQ ID No. 64; and the oligonucleotide pair MA3 and MA4 having the [of] sequences:
MA3: 5'GAA CGC CCG TTG CTG GCC ATT CAC GAG GAG3' SEQ ID NO. 65 and
MA4: 5'GCG CAA CAC GGT CGG ACA GGC CTT CCT CGA3' [.] SEQ ID No. 66.

7. A cloning vector comprising a nucleic acid sequence according to claim 1.

8. Plasmid pMA01 deposited at the CNCM on 28 Aug. 1991 under the no. I-1137.

9. Plasmid pMA02 deposited at the CNCM on 28 Aug. 1991 under the no. I-1138.

10. Oligonucleotide probes specific for a nucleic acid sequence of the strains belonging to the *Mycobacterium avium-intracellulare* complex comprising at least 20 consecutive nucleotides selected from the group consisting of the nucleic sequences according to claim 1.

11. Oligonucleotide probes specific for a nucleic acid sequence of the strains belonging to the *Mycobacterium avium-intracellulare* complex comprising the nucleotide sequences SEQ ID No. 1, SEQ ID No. 2, fragments of these sequences, plasmids containing the nucleotide sequences SEQ ID No. 1, SEQ ID No. 2 or fragments of these sequences, oligonucleotides complementary to nucleic acid sequences SEQ ID No. 1, SEQ ID No. 2 or to fragments of these sequences.

12. Oligonucleotide probes according to claim 11 which are immobilized on a support and are used as capture probes.

13. A method of detection of the presence of strains belonging to the *Mycobacterium avium-intracellulare* complex in a biological sample comprising the steps of:

i) contacting the biological sample with a pair of primers according to claim 5 under hybridization conditions such that the primers specifically hybridize with a nucleic acid sequence from a strain belonging to the *Mycobacterium avium-intracellulare* complex;

ii) amplifying the nucleic acid sequence which has hybridized with the primer pair in the contacting step i);

iii) visualizing the amplified nucleic acid to thereby detect the presence of the strains belonging to the *Mycobacterium avium-intracellulare* complex; and iv) optionally verifying the sequence of the amplified nucleic acid.

14. A kit for the detection of the presence of strains belonging to the *Mycobacterium avium-intracellulare* complex in a biological sample comprising:

an oligonucleotide primer pair according to claim 4;

reagents necessary for carrying out an amplification of a nucleic acid of strains belonging to the *Mycobacterium avium-intracellulare* complex;

optionally a component which makes it possible to verify the detection of the presence of strains belonging to the *Mycobacterium avium-intracellulare* complex.

15. The method according to claim 13 wherein the detection of the presence of strains belonging to the *Mycobacterium avium-intracellulare* complex is verified by specific probe hybridization, by sequencing or by restriction site analysis.

16. The kit according to claim 14 wherein said component which makes it possible to verify the detection of the presence of strains belonging to the *Mycobacterium avium-intracellulare* complex is an oligonucleotide probe specific for a nucleic acid sequence of the strains belonging to the *Mycobacterium avium-intracellulare* complex comprising at least 20 consecutive nucleotides from a nucleic acid sequence which hybridizes specifically with a genomic nucleic acid sequence of the strains belonging to the *Mycobacterium avium-intracellulare* complex, said nucleic acid sequence being selected from the group consisting of the nucleotide sequence SEQ ID No. 1, the nucleotide sequence SEQ ID No. 2, sequences complementary to these, and fragments thereof which specifically hybridize to only the *Mycobacterium avium-intracellulare* complex.

17. An oligonucleotide primer pair according to claim 4 comprising a pair of oligonucleotides whose sequences are selected from the group consisting of the nucleotide sequences represented in FIG. 1.

* * * * *